US012431986B2

United States Patent
Zoss et al.

(10) Patent No.: US 12,431,986 B2
(45) Date of Patent: Sep. 30, 2025

(54) NETWORK PHYSICAL LAYER CONFIGURATIONS FOR AMBULATORY PHYSIOLOGICAL PARAMETER MONITORING AND THERAPEUTIC INTERVENTION SYSTEMS

(71) Applicant: Dexcom, Inc., San Diego, CA (US)

(72) Inventors: Daud Abd al-Malik Zoss, San Diego, CA (US); Barry Nicholas Solomon, Dania Beach, FL (US); Cagri Yalcin, San Diego, CA (US); Carl E. Hoffmeier, Solana Beach, CA (US); Hanna Lin, San Diego, CA (US); John Michael Gray, San Diego, CA (US); Joseph J. Baker, Vista, CA (US); Justin E. Cuzens, San Diego, CA (US); Lorenzo Gorospe Subido, San Diego, CA (US); Michael A. Ploof, Del Mar, CA (US); Neel Narayan Shah, Carlsbad, CA (US); Peter C. Simpson, Cardiff, CA (US); Ritwik Ghosh, Northridge, CA (US)

(73) Assignee: Dexcom, Inc., San Diego, CA (US)

( * ) Notice: Subject to any disclaimer, the term of this patent is extended or adjusted under 35 U.S.C. 154(b) by 656 days.

(21) Appl. No.: 17/649,925

(22) Filed: Feb. 3, 2022

(65) Prior Publication Data
US 2022/0255637 A1 Aug. 11, 2022

Related U.S. Application Data

(60) Provisional application No. 63/148,347, filed on Feb. 11, 2021.

(51) Int. Cl.
*H04B 13/00* (2006.01)
*A61B 5/145* (2006.01)
*H04W 4/38* (2018.01)
*H04W 4/80* (2018.01)

(52) U.S. Cl.
CPC ....... *H04B 13/005* (2013.01); *A61B 5/14532* (2013.01); *H04W 4/38* (2018.02); *H04W 4/80* (2018.02)

(58) Field of Classification Search
CPC .............................. H04B 13/005; H04W 4/38
See application file for complete search history.

(56) References Cited

U.S. PATENT DOCUMENTS

| 2002/0138009 A1 | 9/2002 | Brockway et al. |
| 2003/0060162 A1* | 3/2003 | Shinagawa ............. G06F 1/163 455/100 |

(Continued)

FOREIGN PATENT DOCUMENTS

EP 3340865 A1 7/2018

OTHER PUBLICATIONS

Baskiyar S., "A Real-time Fault Tolerant Intra-body Network", Local Computer Networks, Nov. 6, 2002, pp. 235-240.

(Continued)

*Primary Examiner* — Wen W Huang
(74) *Attorney, Agent, or Firm* — Patterson + Sheridan, LLP

(57) ABSTRACT

Certain embodiments herein relate to a physiological parameter monitoring system. The system may include a sensor and sensor electronics connectable to the sensor. The system may also include a transmitter operably connected to the sensor electronics, the transmitter having or being configured to have at least a portion thereof positioned at a first location adjacent to and/or in contact with an external surface of a body of a host during a sensor session, the transmitter further configured to wirelessly transmit sensor information using human body communication. The system may further include a first display device comprising a display and a receiver, the receiver having or being config- (Continued)

ured to have at least a portion thereof positioned at a second location adjacent to and/or in contact with the external surface of the body during the sensor session, the receiver further configured to receive sensor information from the transmitter using human body communication.

13 Claims, 26 Drawing Sheets

(56) References Cited

U.S. PATENT DOCUMENTS

| | | | | |
|---|---|---|---|---|
| 2012/0197350 | A1* | 8/2012 | Roberts | A61B 5/0028 607/60 |
| 2014/0206976 | A1* | 7/2014 | Thompson | G16Z 99/00 600/391 |
| 2017/0244543 | A1* | 8/2017 | Raj | H04L 67/12 |
| 2018/0207429 | A1* | 7/2018 | Reinke | A61N 1/37211 |
| 2018/0351657 | A1* | 12/2018 | Fukuda | H04B 1/1615 |
| 2021/0337608 | A1* | 10/2021 | Buil | H04W 4/029 |
| 2021/0359768 | A1* | 11/2021 | Post | H04J 13/0048 |
| 2022/0142589 | A1* | 5/2022 | Lee | A61B 5/743 |

OTHER PUBLICATIONS

Invitation to Pay Additional Fees and Where Applicable Protest Fee and Partial International Search for Application No. PCT/US2022/070518, mailed May 24, 2022, 16 pages.

* cited by examiner

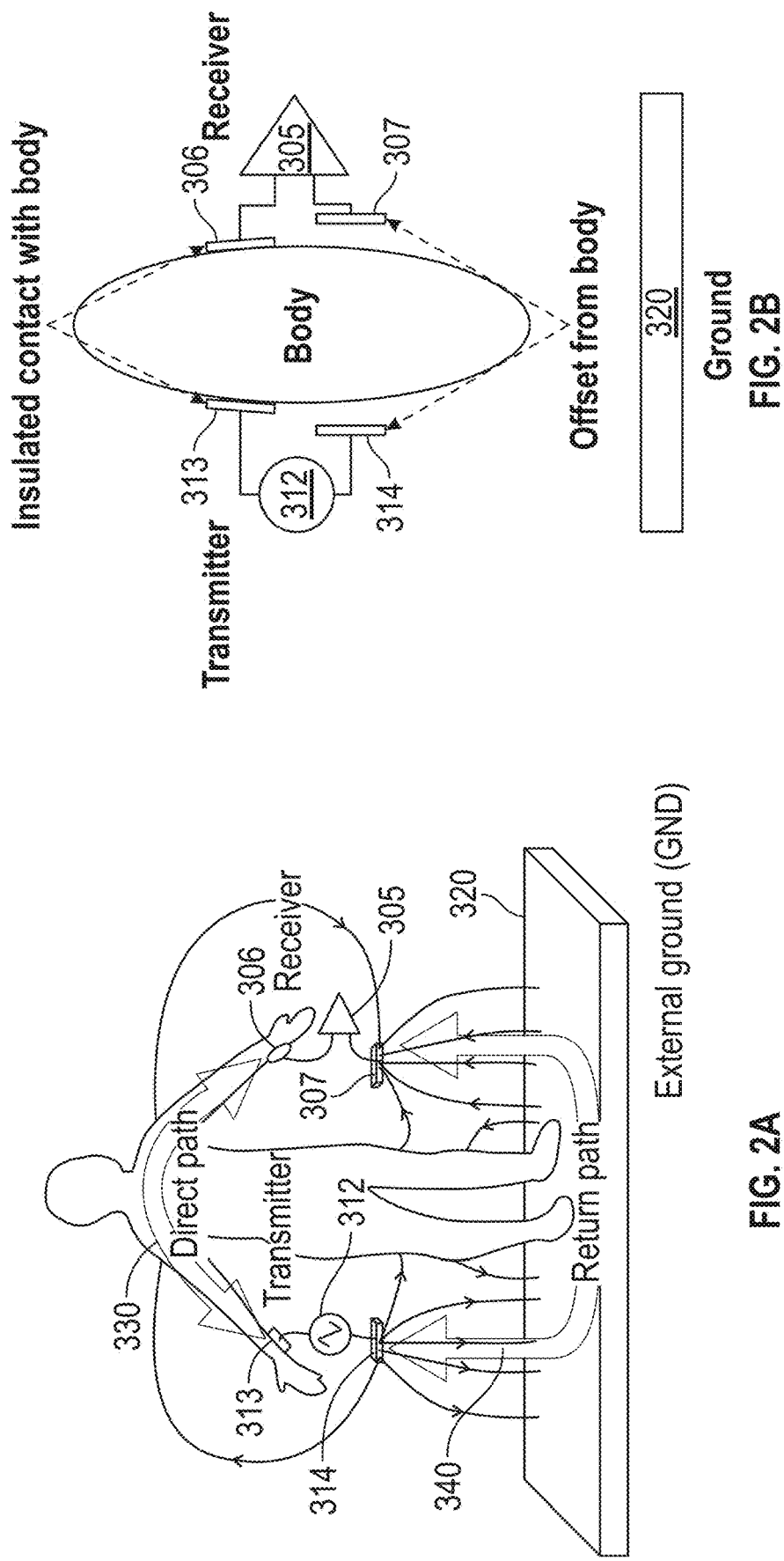

| Configuration | Electrode A Size (mm²) | Electrode B Size (mm²) | Frequency (Mhz) | Distance A to B (mm) |
|---|---|---|---|---|
| 1 | 15 | 270 | 32 | 13 |
| 2 | 15 | 135 | 8 | 25 |
| ③ | 15 | 135 | 20 | 25 |
| 4 | 270 | 270 | 32 | 1 |
| 5 | 135 | 135 | 32 | 1 |
| 6 | 270 | 135 | 20 | 13 |
| 7 | 135 | 270 | 8 | 13 |
| 8 | 15 | 270 | 20 | 1 |
| 9 | 270 | 135 | 32 | 13 |
| 10 | 135 | 15 | 20 | 13 |
| 11 | 270 | 15 | 20 | 1 |
| 12 | 15 | 270 | 32 | 1 |
| 13 | 270 | 15 | 8 | 1 |
| 14 | 135 | 15 | 32 | 25 |
| ⑮ | 135 | 15 | 20 | 25 |
| 16 | 270 | 15 | 8 | 13 |
| 17 | 15 | 15 | 8 | 13 |
| 18 | 135 | 135 | 8 | 1 |

NETWORK PHYSICAL LAYER CONFIGURATIONS FOR AMBULATORY PHYSIOLOGICAL PARAMETER MONITORING AND THERAPEUTIC INTERVENTION SYSTEMS

CROSS-REFERENCE TO RELATED APPLICATIONS

This application claims the benefit of U.S. Provisional Patent Application No. 63/148,347, filed Feb. 11, 2021, the entire contents of which are incorporated by reference herein.

TECHNICAL FIELD

This application relates generally to medical devices such as analyte sensors, including network physical layer configurations for ambulatory physiological parameter monitoring and therapeutic intervention systems.

BACKGROUND

A variety of ambulatory monitors for measuring physiological parameters of a host have been recently developed and are seeing more widespread personal home use. Some of these monitors are fully in vivo implanted in the host. Some have a portion implanted in vivo and a portion extending ex vivo that attaches to external electronics residing on or near the host's body. Some monitors have no in vivo component but reside wholly on the skin or clothing of the host. Ambulatory monitors typically include a sensor that generates a signal indicative of the physiological condition being monitored and sensor electronics operably connected to the sensor for powering sensor operation and processing the sensor output signal.

In addition to monitors comprising sensors and sensor electronics, ambulatory devices for automated or semi-automated medical interventions have also seen increasing personal home use. Ambulatory medical interventions may include, for example, delivery of electrical impulses (e.g., a cardiac pacemaker) or injection of a drug or other therapeutic substance on a schedule or in response to a physiological condition (e.g., an insulin pump). Ambulatory monitors and medical intervention devices may work in conjunction with one another, wherein a medical intervention is wholly or partly controlled by sensor generated data.

These ambulatory monitoring and intervention systems may also include display devices that obtain and process data generated by the sensors during or after use and often include a display to provide information to the host concerning the current value of a sensed physiological parameter or status of an intervention process. These display devices may be handheld, portable, or stationary.

Data communication between the different components of these systems may be wired or wireless. Wireless protocols are often preferred for these applications due to their being user-friendly, comfortable, and less restrictive of host movement. However, commonly used wireless communication techniques may have their own drawbacks in these applications. These drawbacks may include large and variable signal attenuation, poor security, and a generally higher power consumption for a given data rate. Data communication physical layer designs that address these issues are needed.

It should be noted that this Background is not intended to be an aid in determining the scope of the claimed subject matter nor be viewed as limiting the claimed subject matter to implementations that solve any or all of the disadvantages or problems presented above. The discussion of any technology, documents, or references in this Background section should not be interpreted as an admission that the material described is prior art to any of the subject matter claimed herein.

SUMMARY

Human body communication (HBC) and power harvesting techniques are applied to ambulatory physiological monitoring and therapeutic intervention systems.

It is understood that various configurations of the subject technology will become apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

One aspect is a physiological parameter monitoring system comprising: a sensor; sensor electronics operably connected or connectable to the sensor; a transmitter configured to be operably connected to the sensor electronics, the transmitter having or being configured to have at least a portion thereof positioned at a first location adjacent to and/or in contact with an external surface of a body of a host during a sensor session, the transmitter further configured to wirelessly transmit sensor information using human body communication; and a first display device comprising a display and a receiver, the receiver having or being configured to have at least a portion thereof positioned at a second location adjacent to and/or in contact with the external surface of the body of the host during the sensor session, the receiver further configured to wirelessly receive the sensor information from the transmitter using human body communication.

In the above system, the sensor is configured to generate a sensor output signal; the sensor electronics is connected or connectable to the sensor with a wired connection; the transmitter is a primary sensor information transmitter connected or connectable to the sensor electronics with a wired connection; the transmitted sensor information is configured to be generated by or derived from the sensor output signal; the receiver is a primary sensor information receiver; and the primary sensor information receiver is configured to wirelessly receive the sensor information directly from the primary sensor information transmitter.

In the above system, the second location is a wrist of the host. In the above system, the second location is a hand of the host. In the above system, the sensor comprises a glucose sensor. In the above system, the sensor comprises an in vivo portion configured for transcutaneous implantation in the host. In the above system, the in vivo portion of the sensor is configured to be transcutaneously implanted in an upper arm of the host, wherein the first location is the upper arm of the host, and wherein the second location is a wrist of the host. In the above system, the sensor is configured to be transcutaneously implanted in an abdomen of the host, wherein the first location is the abdomen of the host, and wherein the second location is a wrist of the host.

In the above system, the first display device comprises a smart watch. The above system further comprises a second display device. In the above system, the second display device comprises a smartphone. In the above system, the first display device comprises a secondary sensor information transmitter. The above system further comprises a second display device. In the above system, the second display device comprises a secondary sensor information receiver. In the above system, the secondary sensor information transmitter and the secondary sensor information receiver both comprise Bluetooth modules.

Another aspect is a physiological parameter monitoring system comprising: a sensor configured to generate a sensor output signal; sensor electronics connected or connectable to the sensor with a wired connection; a primary sensor information transmitter connected or connectable to the sensor electronics with a wired connection, the primary sensor information transmitter having or being configured to have at least a portion thereof positioned at a first location adjacent to and/or in contact with the epidermis of a body of a host during a sensor session, the primary sensor information transmitter further configured to wirelessly transmit sensor information generated by or derived from the sensor output signal using human body communication; a relay module comprising: a primary sensor information receiver, the primary sensor information receiver having or being configured to have at least a portion thereof positioned at a second location adjacent to and/or in contact with the epidermis of the body of the host during the sensor session, the primary sensor information receiver further configured to wirelessly receive the sensor information from the primary sensor information transmitter using human body communication, and a secondary sensor information transmitter connected or connectable to the primary sensor information receiver with a wired connection and configured to wirelessly transmit sensor information previously received by the primary sensor information receiver from the primary sensor information transmitter; and a first display device comprising a display and a secondary sensor information receiver configured to wirelessly receive the sensor information from the secondary sensor information transmitter using wireless reception.

In the above system, the secondary sensor information transmitter and the secondary sensor information receiver both comprise Bluetooth modules. In the above system, the second location is a wrist of the host. In the above system, the first display device comprises a smartphone.

Another aspect is a physiological parameter monitoring system comprising: a sensor configured to generate a sensor output signal; sensor electronics connected or connectable to the sensor with a wired connection; a first primary sensor information transmitter connected or connectable to the sensor electronics with a wired connection and configured to wirelessly transmit first sensor information generated by or derived from the sensor output signal using human body communication; a second primary sensor information transmitter connected or connectable to the sensor electronics with a wired connection and configured to wirelessly transmit second sensor information generated by or derived from the sensor output signal; a first display device comprising a display and a first primary sensor information receiver configured to wirelessly receive the first sensor information from the first primary sensor information transmitter using human body communication; and a second display device comprising a display and a second primary sensor information receiver configured to wirelessly receive the second sensor information from the second primary sensor information transmitter.

In the above system, the second primary sensor transmitter and the second primary sensor information receiver both comprise a Bluetooth module.

Another aspect is a physiological parameter monitoring apparatus comprising: a sensor configured to generate a sensor output signal relating to a host; sensor electronics operably connected or connectable to the sensor; and a transmitter operably connected or connectable to the sensor electronics, the transmitter comprising: a first conductive contact positioned on a first side of the sensor electronics and operably connected to the sensor electronics; and a second conductive contact positioned on a second side of the sensor electronics and operably connected to the sensor electronics, wherein the sensor electronics is configured to apply a signal across the first and second conductive contacts to wirelessly transmit sensor information generated by or derived from the sensor output signal using human body communication.

In the above apparatus, the sensor electronics, the first conductive contact, and the second conductive contact are affixed to a common substrate. In the above apparatus, the common substrate comprises an adhesive. In the above apparatus, the sensor electronics is positioned between the first conductive contact and the second conductive contact. In the above apparatus, the first conductive contact comprises a metal plate that is or is configured to be capacitively coupled to the epidermis of the host. In the above apparatus, the second conductive contact comprises a metal plate that is or is configured to be capacitively coupled to the epidermis of the host. In the above apparatus, the first conductive contact is covered with a first insulating film and wherein the second conductive contact is covered with a second insulating film. In the above apparatus, the first insulating film is thinner than the second insulating film.

Another aspect is a physiological parameter monitoring system comprising: a sensor configured to generate a sensor output signal; a sensor electronics module operatively connected or connectable to the sensor and comprising a human body communication (HBC) transmitter, the HBC transmitter configured to be positioned at or adjacent to a first portion of a body of a host during a sensor session, the HBC transmitter further configured to wirelessly transmit sensor information generated by or derived from the sensor output signal using human body communication; and a display device comprising an HBC receiver operatively connected to the HBC transmitter and configured to receive the sensor information from the HBC transmitter using human body communication, the HBC receiver configured to be positioned at or adjacent to a second portion of the body of the host during the sensor session, the second portion being different form the first portion.

Another aspect is a method of communicating sensor information using a physiological parameter monitoring system, the method comprising: generating, at a sensor of the physiological parameter monitoring system, a sensor output signal; wirelessly transmitting, at a transmitter of the physiological parameter monitoring system positioned at or adjacent to a first portion of a body of a host, sensor information generated by or derived from the sensor output signal using human body communication; wirelessly receiving, at a receiver of the physiological parameter monitoring system positioned at or adjacent to a second portion of the body of the host, the sensor information from the transmitter using human body communication, the second portion being different form the first portion; and displaying, at a display device of the physiological parameter monitoring system, the received sensor information.

In the above method, the display device comprises a smartwatch.

Another aspect is a physiological parameter monitoring apparatus comprising: a sensor configured to generate a sensor output signal; sensor electronics operably connected or connectable to the sensor; and a transmitter operably connected or connectable to the sensor electronics, the transmitter comprising: a first conductive contact operably connected to the sensor electronics, the first conductive contact having a first area configured for application to a host at a first offset distance away from the skin of the host; and a second conductive contact operably connected to the sensor electronics, the second conductive contact having a second area configured for application to the host at a second offset distance away from the skin of the host, wherein the second area is smaller than the first area, wherein the second offset distance is larger than the first offset distance, and wherein the sensor electronics is configured to apply a signal across the first and second conductive contacts to wirelessly transmit sensor information generated by or derived from the sensor output signal using human body communication.

In the above apparatus, the sensor electronics is positioned substantially between the first conductive contact and the second conductive contact.

Any of the features of an aspect is applicable to all aspects identified herein. Moreover, any of the features of an aspect is independently combinable, partly or wholly with other aspects described herein in any way, e.g., one, two, or three or more aspects may be combinable in whole or in part. Further, any of the features of an aspect may be made optional to other aspects. Any aspect of a method can comprise another aspect of a physiological parameter monitoring system/apparatus, and any aspect of a physiological parameter monitoring system/apparatus can be configured to perform a method of another aspect.

BRIEF DESCRIPTION OF THE DRAWINGS

Various embodiments are discussed in detail in conjunction with the drawings described below, with an emphasis on highlighting the advantageous features. These embodiments are for illustrative purposes only and any scale that may be illustrated therein does not limit the scope of the technology disclosed. These drawings include the following figures, in which like numerals indicate like parts.

FIG. 2A illustrates electrical and/or electromagnetic pathways associated with HBC analyte sensor systems, according to some embodiments.

FIG. 2B also illustrates electrical and/or electromagnetic pathways associated with HBC analyte sensor systems, according to some embodiments.

Figure 1A:
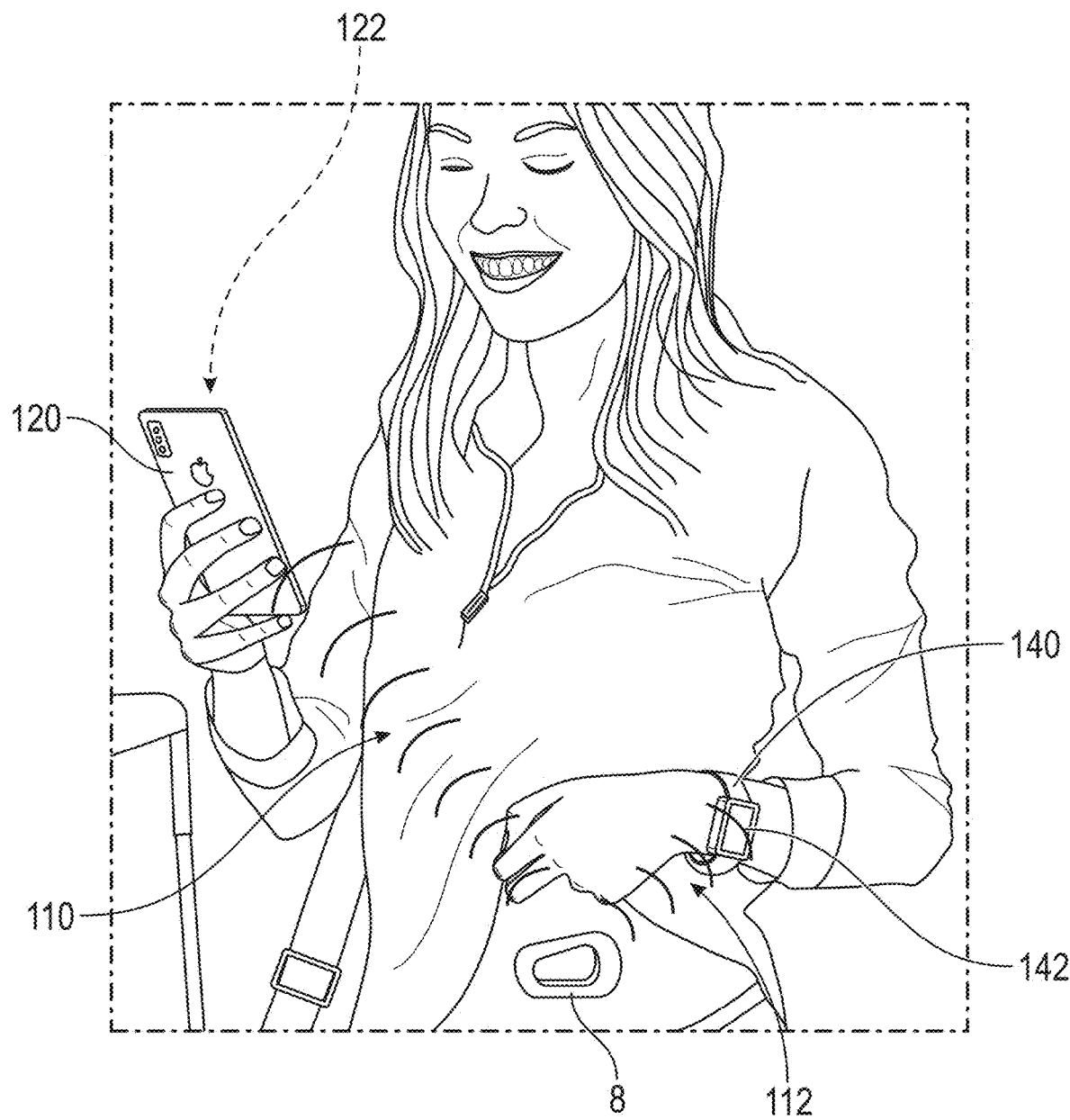
FIG. 1A illustrates aspects of an example analyte sensor system that can be improved by implementing embodiments of the disclosure.

The figures are described in greater detail in the description and examples below, are provided for purposes of illustration only, and merely depict typical or example embodiments of the disclosure. The figures are not intended to be exhaustive or to limit the disclosure to the precise form disclosed. It should also be understood that the disclosure can be practiced with modification or alteration, and that the disclosure can be limited only by the claims and the equivalents thereof.

DETAILED DESCRIPTION

The following description and examples illustrate some exemplary implementations, embodiments, and arrangements of the disclosed technology in detail. Those of skill in the art will recognize that there are numerous variations and modifications of this invention that are encompassed by its scope. Accordingly, the description of a certain example embodiment should not be deemed to limit the scope of the present invention.

Implementations of the technology described herein are directed generally to communication between components of ambulatory physiological monitoring and therapeutic intervention systems. To facilitate an understanding of the various embodiments described, certain terms used herein are defined below.

Definitions

Wired transmission and reception: Signal propagation from a signal source location to a signal receiving location when the signal source location and the signal receiving location are galvanically connected by a solid conductive metallic or semiconducting signal propagation medium. Wired propagation media include metal wire, traces on printed circuit boards, solid state electronic components and integrated circuits, and the like.

Wireless transmission and reception: Signal propagation from a signal source location to a signal receiving location when the signal source location and the signal receiving location are not galvanically connected by a solid conductive metallic or semiconducting signal propagation medium. For example, signal propagation through the air or any other gas, a conductive or non-conductive liquid, an insulating film, a biological material or organism, are all examples of wireless transmission and reception.

Radio transmission and reception: A form of wireless communication between transmit and receive antennas where essentially all the signal energy propagates through an air gap separating the transmit and receive antennas. This form of communication may be far field, where the wavelength of the signal carrier is relatively small compared to the distance between the communicating devices, or near field, where the wavelength of the signal carrier is relatively large compared to the distance between the communicating devices. Far field radio communication is typically implemented using patch antennas or variants thereof, wherein examples include WiFi and Bluetooth. Near field radio communication is typically implemented using coil antennas, wherein examples include NFC and NFMI. Carrier frequencies for both may be typically about 1 MHz to 100 GHz.

Wired Connection: A wired connection exists between a given signal source and a given signal receiver when they are configured and deployed to communicate using wired transmission and reception.

Wireless Connection: A wireless connection exists between a given signal source and a given signal receiver when they are configured and deployed to communicate using wireless transmission and reception.

Sensor: An apparatus configured to generate an output signal indicative of the presence and/or amount of a physiological, environmental, chemical or other substance or condition existing at a location that is at, near, or otherwise related to the sensor location, including but not limited to an analyte sensor, a temperature sensor, a pressure sensor, and a motion sensor.

Sensor information: Any information associated with one or more sensors. Sensor information includes a raw data stream, or simply data stream, of analog or digital signals directly related to a measured signal output from an analyte sensor (or other signal received from another sensor), as well as calibrated and/or filtered raw data. Sensor information may include calibrated data, smoothed data, filtered data, transformed data, and/or any other information associated with a sensor such as sensor ID values, calibration codes, manufacturing information, or the like.

Analyte Sensor: A structure incorporating any mechanism (e.g., enzymatic or non-enzymatic) by which an amount or concentration of an analyte can be quantified. Glucose sensors used to monitor glucose concentration in diabetics are a common example. Some glucose sensors utilize a membrane that contains glucose oxidase that catalyzes the conversion of oxygen and glucose to hydrogen peroxide and gluconic acid. Using this reaction, an electrode can be used to monitor conductivity due to hydrogen peroxide generation to measure glucose concentration. Fluorescence detection may also be used to quantify glucose concentrations using fluorescent molecules that have glucose concentration dependent fluorescence. Other analytes such as lactate, hormones, and the like can be quantified with analogous chemical and/or optical methods.

Sensor electronics: Analog and/or digital circuits having or configured to have a wired connection to one or more sensors and that provide power for sensor operation and/or receive output signals from the one or more sensors for processing and/or storage and/or transmission to another device. For an analyte sensor, sensor electronics may include a potentiostat and other sensor current acquisition circuits such as switches, buffers, filters, and the like, an A/D converter, and memory for storage of digital data indicative of sensor current magnitude.

Primary sensor information transmitter: A communication device having or configured to have a wired connection to sensor electronics that is configured and deployed to transmit sensor information using wireless transmission that is generated by or derived from signals output from one or more sensors that have or are configured to have a wired connection to the sensor electronics.

Sensor electronics module: A combination of sensor electronics, one or more primary sensor information transmitters, and one or more wired connections therebetween. The components of a sensor electronics module are generally but not necessarily enclosed in, coupled to, or otherwise mechanically associated with a housing or other mounting structure that has features for fixation to the body or clothing of a host.

Primary sensor information receiver: A communication device configured and deployed to receive sensor information from a primary sensor information transmitter using wireless reception.

Secondary sensor information transmitter: A communication device configured and deployed to transmit sensor information that was previously transmitted by a primary sensor information transmitter using wireless transmission. A secondary sensor information transmitter can also be a primary sensor information transmitter (and vice versa) for sensor information generated by or derived from signals output from one or more sensors it may have a wired connection to.

Secondary sensor information receiver: A communication device configured and deployed to receive sensor information from a secondary sensor information transmitter using wireless reception. A secondary sensor information receiver can also be a primary sensor information receiver (and vice versa) if it is configured and deployed to communicate with both a secondary sensor information transmitter and a primary sensor information transmitter.

Relay module: A combination of one or more primary sensor information receivers and one or more secondary sensor information transmitters and a set of one or more wired connections therebetween. As with a sensor electronics module, a relay module is generally but not necessarily enclosed in, coupled to, or otherwise mechanically associated with a housing or other mounting structure that has features for fixation to the body or clothing of a host.

Power transmitter: An apparatus configured and deployed for transmitting wireless signals suitable for energy harvesting by another device. The signals may or may not also function as a data transfer mechanism in addition to a power transfer mechanism such that primary and secondary sensor information transmitters may also be power transmitters.

Power receiver: An apparatus configured and deployed to route at least some of the energy of received electric and/or magnetic fields to an energy storage device such as a capacitor and/or a rechargeable battery. A power receiver may utilize all or part of a primary sensor information receiver or a secondary sensor information receiver to perform an energy capture function.

Display device: A combination of a display and one or more primary sensor information receivers and/or one or more secondary sensor information receivers with a wired connection therebetween that is configured to display sensor information received by the primary and/or secondary sensor information receivers. Display devices may, for example, be multi-functional smart phones or smart watches or may be dedicated devices specifically made for use with a monitoring system.

Operably connected: One or more components of a device or system being linked to another component(s) of the device or system in a manner that allows transmission of signals between the components. The term operably connected includes a capacity for signal transmission or exchange either with mechanical contact (e.g., a wired connection) or without mechanical contact (e.g., a wireless connection).

Determining: Calculating, computing, processing, deriving, investigating, retrieving, looking up (e.g., looking up in a table, a database or another data structure), ascertaining, estimating, detecting, and the like. "Determining" may also include receiving (e.g., receiving information), accessing (e.g., accessing data in a memory) and the like. Also, "determining" may include resolving, selecting, choosing, calculating, deriving, establishing or the like. Determining also includes classifying a parameter or condition as present or not present, and/or meets a predetermined criterion, including that a threshold has been met, passed, exceeded, and so on.

Substantially: Largely but not necessarily wholly that which is specified such that at least most of the practical effect or purpose of that which is specified is maintained.

Transcutaneous: Located under the epidermis of a subject, including locations in the dermis, hypodermis, and/or underlying muscle tissue, but excluding intravenous or intraarterial locations.

Transcutaneous sensor: A sensor configured for making measurements when in a transcutaneous location, regardless of the method of placing the sensor in the transcutaneous location.

Non-invasive: Without piercing the epidermis.

Non-invasive sensor: A sensor capable of making measurements without piercing the epidermis. Sensors configured for use in natural cavities such as the mouth are included in the term non-invasive sensors.

Smartphone: A portable electronic device that wirelessly supports communication services including one or both of voice and text and Internet access capability.

Bluetooth (BLE) module—An electronic circuit in one or more physical packages that in operation is configured to wirelessly communicate using radio transmission and reception with other electronic circuits in a manner satisfying those interoperability requirements relevant to the communications of any version of a Bluetooth Core Specification (or related specification derived such as IEEE802.15.1) that is adopted by the Bluetooth Special Interest Group or any successor standards development organization.

Near field communication (NFC) module and Near field magnetic induction (NFMI) module: An electronic circuit in one or more physical packages that is configured to wirelessly communicate using near field radio transmission and reception with other electronic circuits using inductive coupling. NFC operates at 13.56 MHz. NFMI operates at 10.5 MHz.

Human Body Communication (HBC): Signal communication from a transmitting location on or near a host body to a receiving location that is also on or near the host body, wherein signal energy propagation from the transmitting location to the receiving location is substantially provided by electric current, electric field flux, and/or magnetic field flux penetrating into and/or through host body tissue. HBC is a form of wireless transmission and reception. HBC is one of three standardized physical layer configurations described in IEEE802.15.6 for use in so-called body area networks. The HBC physical layer in this IEEE standard uses a carrier of 21 MHz. An HBC signal may be galvanic, capacitive, inductive, or hybrid.

Galvanic HBC: HBC that primarily relies on modulating charge migration within host body tissue such that forward and return current paths created in the host body tissue operably couple the HBC transmitter and the HBC receiver.

Capacitive HBC: HBC that primarily relies on modulating an electric field flux within host body tissue to operably couple the HBC transmitter and the HBC receiver.

Inductive HBC: HBC that primarily relies on modulating a magnetic field flux within host body tissue to operably couple the HBC transmitter and the HBC receiver.

Hybrid HBC: HBC that utilizes a combination of galvanic HBC, capacitive HBC, and inductive HBC to operably couple the HBC transmitter and the HBC receiver.

Mobile App: A mobile app is a software program that can execute on smartphone operating systems such as iOS and Android. Although a mobile app is generally designed for operation on handheld smartphones, a mobile app can be executed on non-mobile devices that are running an appropriate operating system.

Server: Processing hardware coupled to a computer network having network resources stored thereon or accessible thereto that is configured with software to respond to client access requests to use or retrieve the network resources stored thereon. Multiple independent instances of server software programs can be executing simultaneously on the same processing hardware. Each such instance would constitute a server.

Internet: The globally interconnected system of computers and computer networks that evolved from ARPANET and NSFNET over the late 1980s and early 1990s that may utilize TCP/IP network communication protocols.

Web Site—A collection of network resources including at least some web pages that share a common network resource identifier portion, such as a set of web pages with URLs sharing a common domain name but different pathnames.

Web Server—A server that includes functionality for responding to requests issued by browsers to a network, including, for example, requests to receive network resources such as web pages. Currently, browsers and web servers format their requests and responses thereto in accordance with the HyperText Transfer Protocol (HTTP) promulgated by the IETF and W3C. In some embodiments, a web server may also be a content server.

World Wide Web—The collection of web pages stored by and accessible to computers running browsers connected to the Internet that include references to each other with internal linking syntax.

Overview

Systems and devices described herein are configured to use human body implanted and/or affixed sensors of physiological parameters, and to communicate sensor information utilizing human body communication (HBC). For example, as will be described in connection with several figures, one or more systems use body tissue of the host as the primary medium for signal propagation between a transmitter and a receiver within the system.

Many communication protocols that have conventionally been used in ambulatory monitoring systems are unsuitable for HBC. For example, far-field protocols such as Bluetooth, Zigbee, ANT, and the like typically use modulated carriers of 2 gigahertz (GHz) or more. The human body is highly absorbing to electromagnetic radiation at these frequencies. Propagation from a transmitter to a receiver with these protocols will not propagate through the body but will only propagate away from or around the body, rendering these protocols unsuitable for using body tissue as a signal transmission medium. Furthermore, communication at such relatively high frequencies requires significant power, producing high battery drain, which along with associated requirements for high-profile antennas, forces a relatively large size on wearables for the host.

NFC technology, which is regularly used in smart credit cards, inventory RFID tags, and the like has been proposed and commercially utilized for sensor information communication. NFC uses two coils as a transmit and receive antenna respectively. The coupling mechanism for data transfer is magnetic induction from the transmit coil to the receive coil, normally using a carrier of 13.56 megahertz (MHz). During data communication, the receive antenna is separated from the transmit antenna by an air gap of typically 10 cm or less through which the signal propagates. Therefore, this technology has also not been utilized for use with the human body as a signal propagation medium.

NFMI has been implemented in an HBC system for wireless communication through a human head between hearing aids and audio earbuds under the trade name MiGlo™ Like NFC, NFMI also couples coil antennas with magnetic induction, but at a frequency of approximately 10.5 MHz. The NFMI protocol has not been used for physiological monitoring systems.

Described below are embodiments of physiological monitoring apparatus and systems using various forms of HBC. Novel physical configurations for transmitters and receivers in physiological monitoring systems are provided. System embodiments may operate at frequencies under, for example, approximately 120 MHz, in some embodiments, approximately 8 MHz-approximately 32 MHz, in some embodiments, approximately 5 MHz-approximately 25 MHz, and in some embodiments, approximately 10 MHz or 20-21 MHz, depending on the specific implementation. These frequencies are merely examples and other frequencies are also possible. These ranges have desirable low path loss through host body tissue and allow for low energy consumption during such communications. In turn, such HBC configurations may provide lower battery output currents, a flexible wearable that conforms to the skin of the user, and reliable sensor information communication between components. These features allow the construction of physiological monitoring systems and components having smaller batteries or no batteries as well as reduced height and/or form factor of wearables for the user.

Embodiments

Many specific physiological monitoring system embodiments described herein relate to systems for monitoring blood glucose concentrations in a diabetic host. For this purpose, a variety of non-invasive, transcutaneous, and/or implantable electrochemical sensors have been developed and are commercially available for continuously detecting and/or quantifying blood glucose values. These devices generally include (1) a transcutaneous glucose sensor, (2) a sensor electronics module connected or connectable to the transcutaneous sensor that is attached to the skin of the host and (3) a display device. The sensor electronics module may transmit raw, minimally processed, or fully processed and calibrated sensor information for further processing (if necessary) and display to the host. The sensor electronics module and the display device may be operably connected by a wireless communication protocol, with Bluetooth being the most common. Although this form of physiological monitoring system provides an example for discussion below, the apparatus and operational methods described are applicable to any monitored characteristic of a host.

Figure 1B:
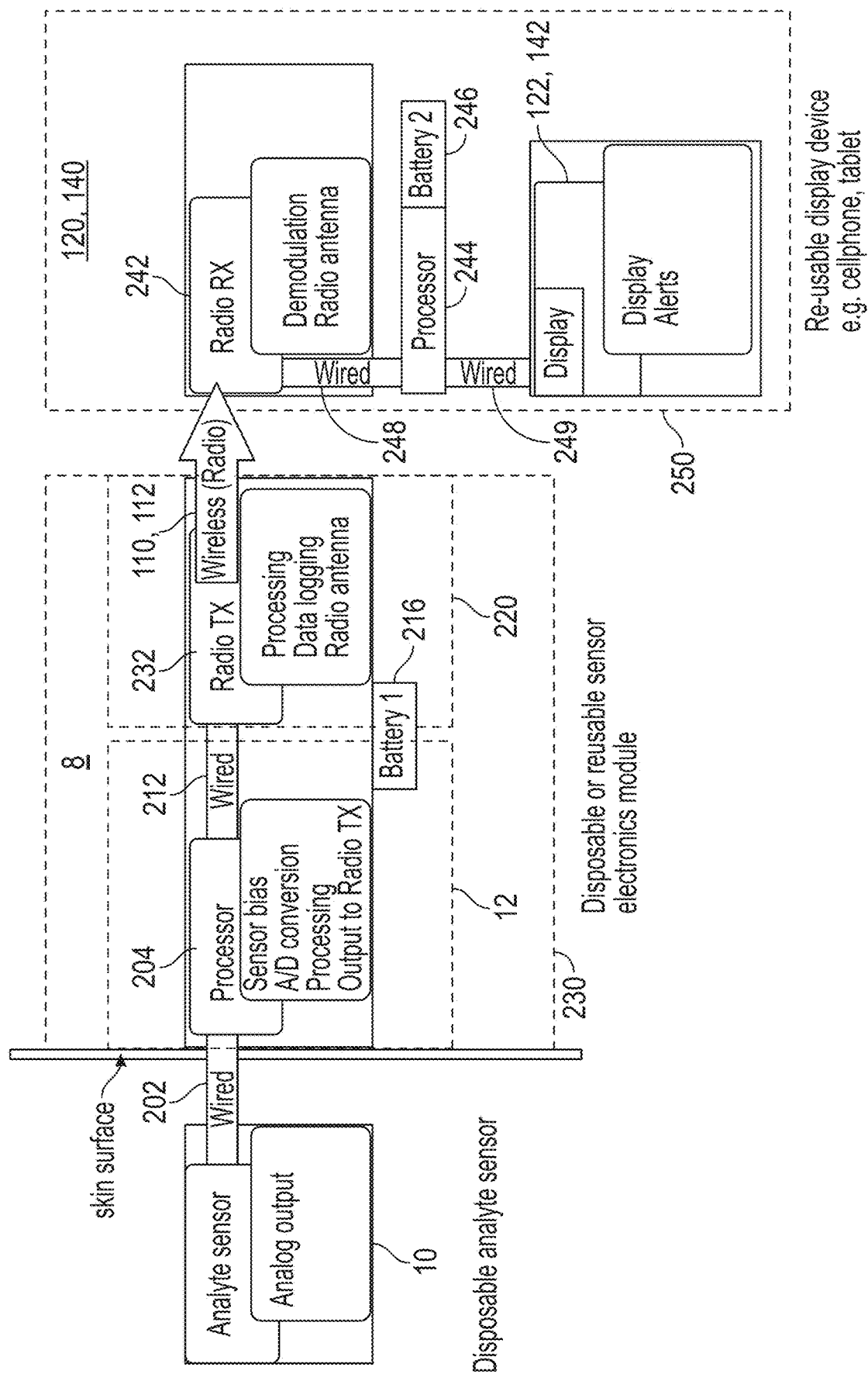
FIG. 1B illustrates a schematic block diagram of the analyte sensor system configured to wirelessly communicate analyte data of FIG. 1A.

FIG. 1A illustrates aspects of an example analyte sensor system that can be improved by implementing embodiments of the disclosure. FIG. 1B illustrates a schematic block diagram of the analyte sensor system configured to wirelessly communicate analyte data of FIG. 1A. With reference now to FIGS. 1A and 1B, in some embodiments, analyte sensing systems may include an analyte sensor 10 configured to continuously or periodically generate a signal indicative of a concentration of an analyte of a host. In some embodiments, analyte sensor 10 includes a continuous glucose sensor, for example, a subcutaneous, transcutaneous, or intravascular device.

A glucose sensor, as used herein, can be any device capable of measuring the concentration of glucose. A glucose sensor can use any known method, including invasive, minimally invasive, and non-invasive sensing techniques (e.g., fluorescent monitoring), to provide a data stream indicative of the concentration of glucose in a host. The data stream is typically a raw data signal, which is converted into a calibrated and/or filtered data stream that is used to provide a useful value of glucose to a user, such as a patient or a caretaker (e.g., a parent, a relative, a guardian, a teacher, a doctor, a nurse, or any other individual that has an interest in the wellbeing of the host).

In certain embodiments, analyte sensor 10 is an implantable analyte sensor such as described with reference to U.S. Pat. No. 8,001,067 and U.S. Patent Application Publication No. US-2005-0027463-A1. In some embodiments, analyte sensor 10 is a transcutaneous analyte sensor having an in vivo portion and an ex vivo portion, such as described with reference to U.S. Patent Application Publication No. US-2006-0020187-A1. In some embodiments, analyte sensor 10 is configured to be implanted in a host vessel or extracorporeally, such as is described in U.S. Patent Application Publication No. US-2007-0027385-A1, co-pending U.S. Patent Application Publication No. US-2008-0119703-A1 filed Oct. 4, 2006, U.S. Patent Application Publication No. US-2008-0108942-A1 filed on Mar. 26, 2007, and U.S. Patent Application No. US-2007-0197890-A1 filed on Feb. 14, 2007. In some embodiments, the analyte sensor includes a transcutaneous sensor such as described in U.S. Pat. No. 8,565,509 to Say et al., for example. In some embodiments, analyte sensor 10 includes a subcutaneous sensor such as described with reference to U.S. Pat. No. 8,579,690 to Bonnecaze et al. or U.S. Pat. No. 8,484,046 to Say et al., for example. In some embodiments, the analyte sensor includes a refillable subcutaneous sensor such as described with reference to U.S. Pat. No. 8,512,939 to Colvin et al., for example. The analyte sensor 10 can include an intravascular sensor such as described with reference to U.S. Pat. No. 8,477,395 to Schulman et al., for example. The analyte sensor 10 can include an intravascular sensor such as described with reference to U.S. Pat. No. 8,424,847 to Mastrototaro et al., for example. All of the U.S. patents and publications described in this paragraph are incorporated herein by reference in their entirety.

The system may further include a sensor electronics module 8, which comprises sensor electronics 12 operably connected to a telemetry module 220 with a wired connection 212. The sensor electronics module 8 is operably connected to at least one analyte sensor 10 during a sensor session. In certain embodiments, sensor electronics 12 includes electronic circuitry associated with measuring and processing the analyte sensor data, which may include prospective algorithms associated with processing and calibration of the sensor data. Sensor electronics 12 can be connected with a wired connection 202 to a transcutaneous analyte sensor 10. Sensor electronics 12 can be integral with, non-releasably attached to, or releasably attached or attachable to transcutaneous analyte sensor 10. The components of the sensor electronics module may be enclosed in or otherwise attached to a housing or holder 230 configured for attachment to the skin or clothing of a host during a sensor session.

The sensor electronics 12 can include hardware, firmware, and/or software that enables measurement of levels of the analyte. For example, sensor electronics 12 can include a potentiostat (not shown), a battery 216 for providing power to components of the sensor electronics, other components useful for signal processing (e.g., a processor and in some cases, an analog front end (AFE) comprising at least analog-to-digital (A/D) conversion circuitry), and data storage (e.g., a memory).

The telemetry module 220 (e.g., radio transmitter or transceiver) may be operably connected to the sensor electronics 12 by a wired connection 212 for transmitting data from sensor electronics module 12 to one or more display devices 120, 140 with radio transmission circuitry 220 such as 4G LTE, WiFi, NFC and/or BLE.

The sensor electronics 12 can be affixed to a rigid or flexible printed circuit board (PCB), or the like, and can take a variety of forms. For example, the sensor electronics 12 can at least in part take the form of an integrated circuit (IC), such as an application-specific integrated circuit (ASIC), a microcontroller, and/or any other type of processor 204. In some embodiments, sensor electronics 12 are configured with signal processing algorithms (programming), for example, configured to filter, calibrate, transform and/or execute other algorithms on sensor data. Examples of systems and methods for processing sensor analyte data are described in more detail herein and in U.S. Pat. Nos. 7,310,544 and 8,931,327 and U.S. Patent Publication Application Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entirety for all purposes. Some or all of the components of telemetry module 220 can be affixed to the same PCB as the sensor electronics 12, with the wired connection 212 formed by circuit components and conductive traces on or in the PCB connecting the components.

The sensor electronics module 8 can further comprise an adhesive pad, placed before, during or after sensor 10 is inserted to ensure adhesion, and optionally to ensure an airtight seal or watertight seal around a wound exit-site (or sensor insertion site) (not shown). Appropriate adhesive pads can be chosen and designed to stretch, elongate, conform to, and/or aerate the region (e.g., host's skin). Configurations and arrangements can provide water resistant, waterproof, and/or hermetically sealed properties associated with the mounting unit/sensor electronics module embodiments described herein.

The analyte sensor system can also include one or more display devices 120 and 140 according to certain aspects of the present disclosure. A display device 120, 140 may comprise a telemetry module comprising a radio receiver 242, a display 122, 142, a processor or controller 244 and a battery 246. Wired connections 248, 249 connect the processor 244, display 122, 142, and primary receiver 242, all of which may be contained within a common housing 250. The sensor electronics module 8 can be in wireless communication with one or more display devices 120, 140.

One or more of display devices 120, 140 can be further configured to transmit data, which in some cases may be raw or, alternatively, processed analyte data or other sensor information, to one or more other devices, for example one or more of the other display devices 120, 140.

Display devices 120, 140 are configured for displaying (and/or alarming) sensor information derived at least in part from data transmitted by sensor electronics module 8 (e.g., in a series of data packages that are transmitted to the appropriate display device(s)). Accordingly, each of display devices 120, 140 so-configured can also include a respective display such as a touchscreen display 122, 142 for displaying sensor information, analyte data and/or other data or alarms to a user and/or for receiving inputs from the user. For example, a graphical user interface can be presented to the user for such purposes. In some embodiments, the display devices can include other types of user interfaces such as voice user interface instead of or in addition to a touchscreen display for communicating sensor information to the user of the display device and/or receiving user inputs.

The system of FIGS. 1A and 1B uses radio transmission and reception 110, 112 such as Bluetooth to transfer sensor information from the sensor electronics module 8 to one or more display devices 120, 140. These circuits can require significant power to operate and accordingly a relatively large battery 216 may be required.

FIG. 2A illustrates electrical and/or electromagnetic pathways associated with HBC analyte sensor systems, according to some embodiments. FIG. 2B also illustrates electrical and/or electromagnetic pathways associated with HBC analyte sensor systems, according to some embodiments. In some embodiments described herein, a different wireless communication method may be used for some portions of the communication between components that may require much less power than the embodiments of FIGS. 1A and 1B, as illustrated conceptually in FIGS. 2A and 2B. In these embodiments, an analyte sensor system includes a transmitter 312 having a first insulated transmit electrode 313 disposed closely adjacent to the tissue of the host and a second insulated transmit electrode 314 offset from tissue of the host by a predetermined distance compared to first insulated contact 313. The analyte sensor system further includes a receiver 305 having a first insulated receive electrode 306 disposed against the tissue of the host and a second insulated receive electrode 307 offset from tissue of the host by a predetermined distance compared to first receive electrode 306.

Figure 3A:
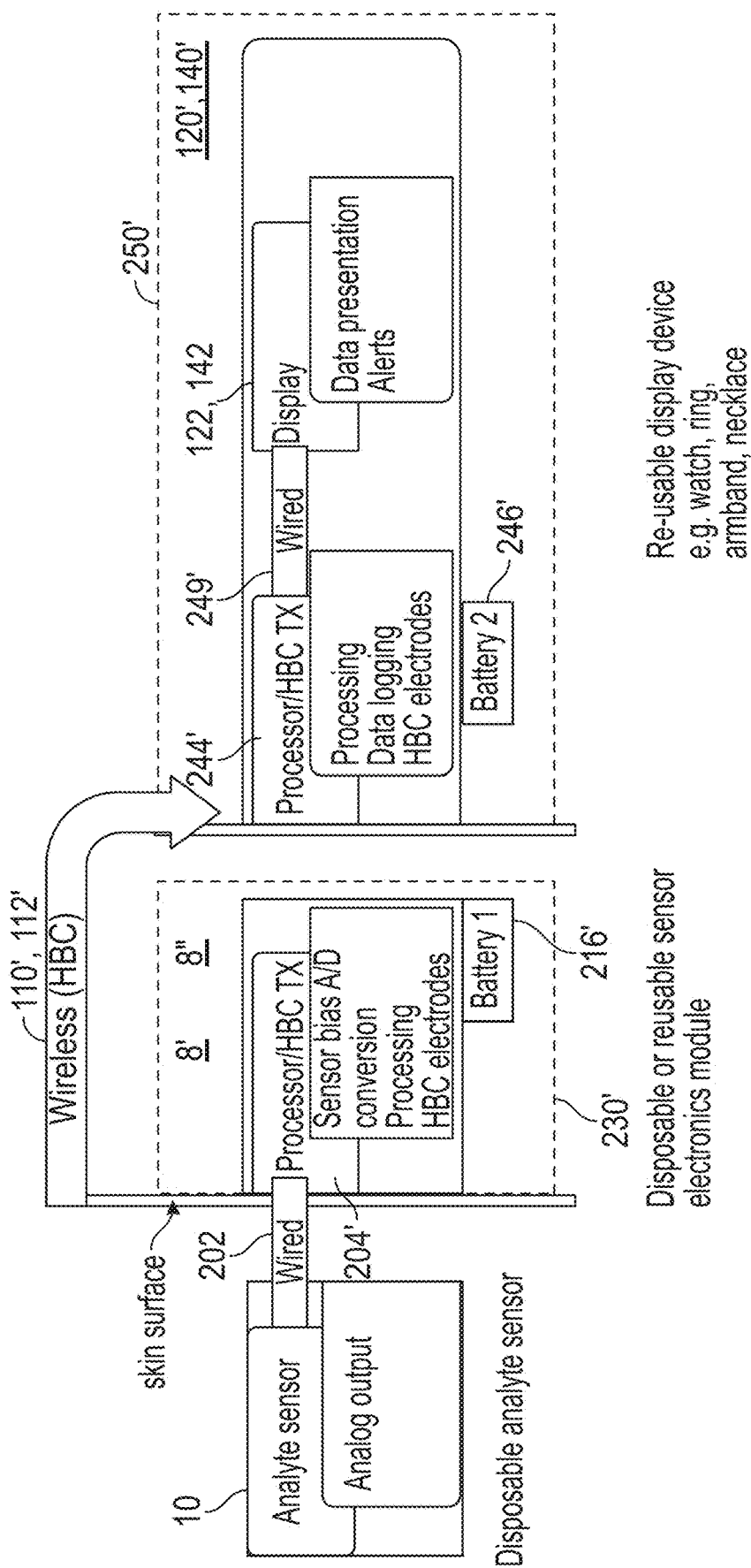
FIG. 3A illustrates a schematic block diagram of an HBC analyte sensor system, according to some embodiments.

As illustrated in FIGS. 2A and 2B, the analyte sensor system makes use of a human body communication (HBC) technique since the tissue of the host forms the main transmission medium for wireless signals between transmitter 312 and receiver 305, with the specific paths traversed by the wireless signals dependent on the specific configuration of the electrodes of transmitter 312, receiver 305, of the tissue of the host, and of other capacitive aspects of the local, outside environment. As illustrated in FIG. 2A, the capacitive coupling arrangement establishes transmission paths for the wireless signal including a path 330 through tissue between first insulated electrode 313 of transmitter 312 and first insulated electrode 306 of receiver 305, and a second path 340 that is more coupled with the outside environment local to the host, e.g., earth ground 320, etc., between transmit electrode 314 of transmitter 312 and receive electrode 307 of receiver 305. The lined arrows extending from transmit electrode 314 to receive electrode 307 in FIG. 3A illustrate example electric field lines generated by the electrostatic potential associated with the capacitive coupling, passing through the local outside environment between transmitter 312 receiver 305 and an external common ground therebetween. Accordingly, first insulated contacts 313 and 306 of respective transmitter 312 (e.g., primary transmitter) and receiver 305 function as signal electrodes, while second insulated contacts 314 and 307 of respective primary transmitter 312 and receiver 305 function as ground electrodes.

In some embodiments, receiver 305 can alternatively replace first and second receive electrodes 306, 307 with an insulated high-Q magnetic antenna or pickup coil configured to generate a suitable electrical potential across its terminals under the influence of the electrostatic potential signal generated by transmitter 312 and propagated through tissue of the host. In these embodiments, using insulated high-Q magnetic pickup coil in place of first and second receive electrodes 306, 307 may provide increased signal to noise ratio for the signal received by receiver 305 and mitigates potential issues associated with low signal levels. These embodiments can allow proper sensing and/or pickup of HBC signals when receiver 305 is disposed farther up a same arm or on an opposite arm compared to transmitter 312, or even when receiver 305 is disposed farther away from transmitter 312 on the abdomen of the host, depending on the physical dimensions of the host and/or of insulated high-Q magnetic pickup coil.

Achievable communication ranges and data rates between transmitter 312 and receiver 305 may vary, and depend on frequency of operation, data symbol rate, modulation type, physiologic factors of the host, limits on transmit power of transmitter 312, and on environmental capacitive factors of the local outside environment. Accordingly, such capacitive coupling can be suitable for higher data rates but can be sensitive to capacitively couplable devices or objects in the immediate environment. Generally, example frequency ranges for such communication may be less than or equal to approximately 120 MHz, in some embodiments, approximately 8 MHz-approximately 32 MHz, in some embodiments, approximately 5 MHz-approximately 25 MHz, and in some embodiments, approximately 20 MHz-approximately 21 MHz.

Figure 3B:
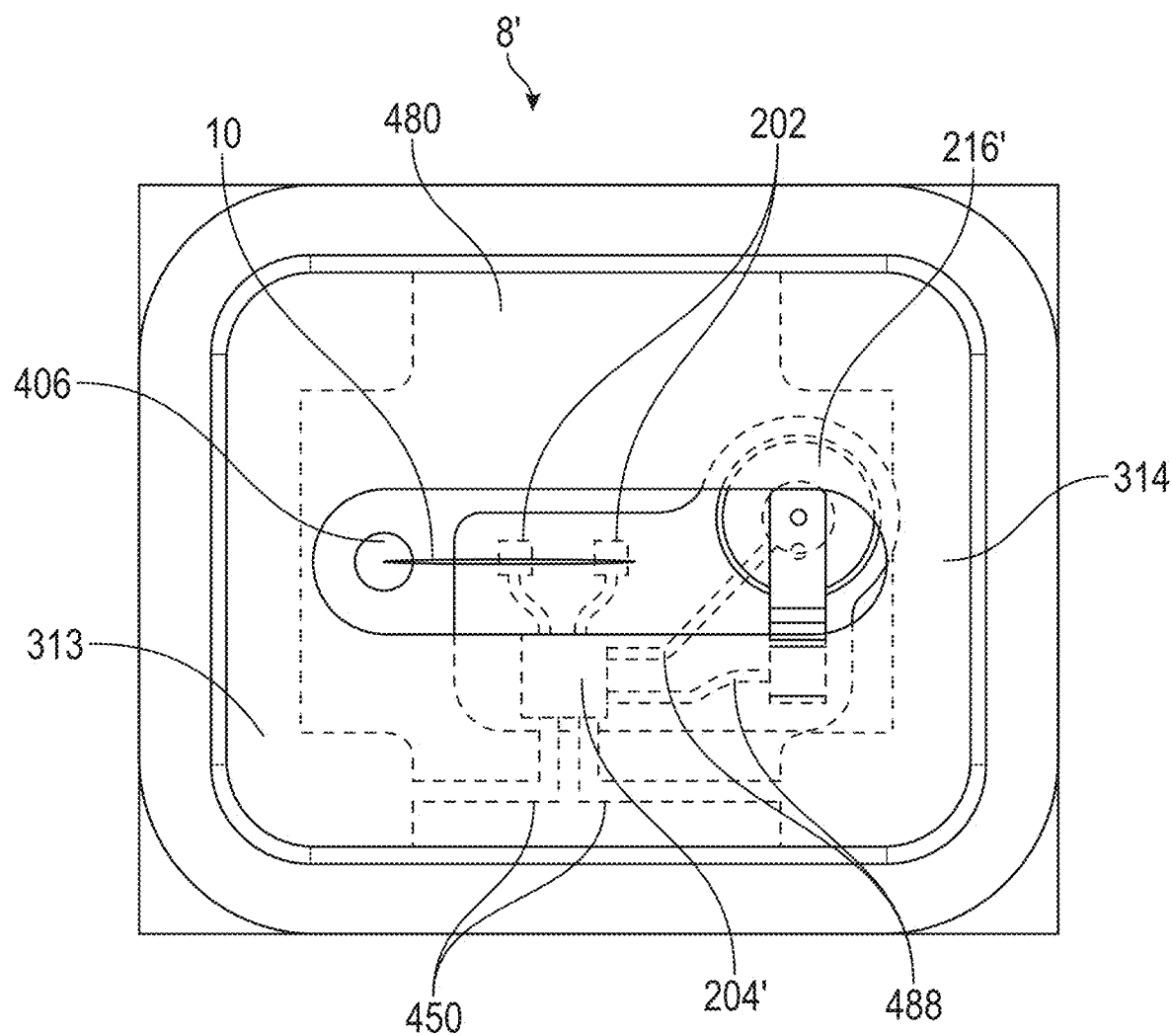
FIG. 3B illustrates an example of a component and connection layout for a sensor electronics module according to some embodiments implementing the architectures of FIG. 3A.
Figure 3C:
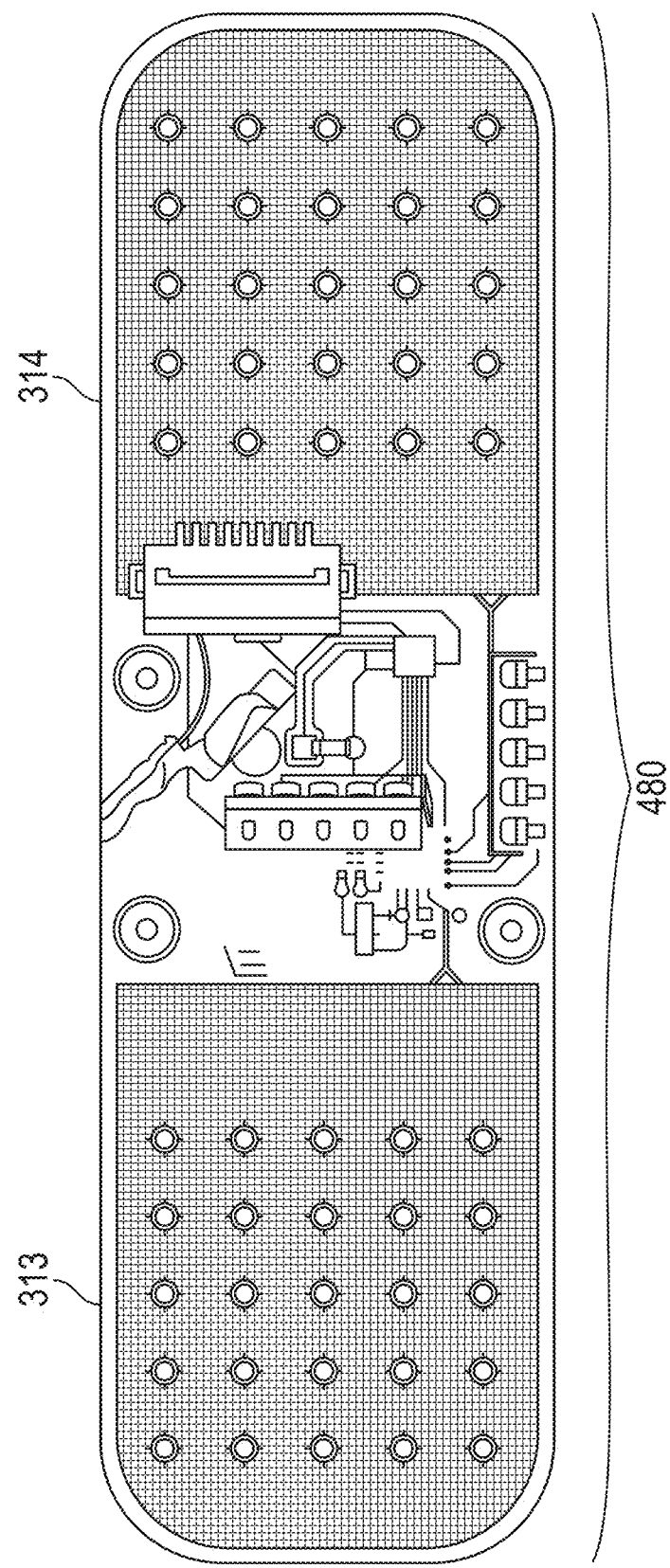
FIG. 3C shows a top view of a sensor electronics module configured to wirelessly communicate analyte data through tissue of a host, according to some embodiments.

FIG. 3A illustrates a schematic block diagram of an HBC analyte sensor system, according to some embodiments. FIG. 3B illustrates an example of a component and connection layout for a sensor electronics module according to some embodiments implementing the architectures of FIG. 3A. FIG. 3C shows a top view of a sensor electronics module configured to wirelessly communicate analyte data through tissue of a host, according to some embodiments. FIGS. 3D-3H respectively illustrate first to fifth analyte sensor systems each comprising a sensor electronics module and a display device configured for human body communication, according to some embodiments. A specific implementation of an analyte sensing system configured for HBC communication will now be described in more detail in connection with FIGS. 3A through 3H. FIG. 3A shows one example of a sensor electronics module 8' configured to wirelessly communicate sensor information through tissue using HBC communication to a display device 120', 140', according to some embodiments.

As shown in FIG. 3A, sensor electronics module 8' is operably coupled to an analyte sensor 10 with a wired connection 202 similar to that shown in FIG. 1B. However, in FIG. 3A, the communication channels 110', 112' for wireless communication between the sensor electronics module 8' and display device 120', 140' are HBC communication channels which may be configured in accordance with the principles described above with reference to FIGS. 2A and 2B. As with the system of FIG. 1B, in some embodiments, battery (1) 216' may be disposable after one sensor session along with the rest of the sensor electronics module 8' and not intended to be recharged for further use with a new sensor 10. In some embodiments, battery (2) 246' may be rechargeable so that the display device 120', 140' is reusable for many sensor sessions. In some embodiments, battery (1) 216' may be rechargeable (e.g., periodically connected to a charging device for wired or wireless charging) so that the sensor electronics module 8' is reusable with one or more new replaceable sensors 10.

FIG. 3B shows one possible embodiment of a component layout for the sensor electronics module 8' of FIG. 3A. In FIG. 3B, sensor electronics module 8' is illustrated as being operatively coupled to sensor 10, which may be disposed through an aperture 406 in PCB 480 and provides an electrical signal proportional to a detected level of the analyte (e.g., glucose) within the host. Contacts and electrical traces 202 are configured to provide a wired connection for the analog signal from sensor 10 to a processor, microcontroller, ASIC, or the like 204', similar in part to the processor 204 as previously described in connection with FIG. 1B, and which may comprise electronics required for conversion of the analog signal from sensor 10 into a signal suitable for transmission via first and second transmit electrodes 313, 314 through host tissue, via HBC, to a display device 120', 140'. The signal can be provided to first and second transmit electrodes 313, 314 via respective electrical traces 450 disposed on or within flexible PCB 480.

The sensor electronics module 8' can further include a battery 216'. While battery 216' can be any suitable type of battery (e.g., a coin battery), in some embodiments, battery 216' may comprise an even smaller, lower-profile battery that is printed onto PCB 480. In other embodiments, battery 216' may have a substantially flat top and/or bottom surface and may be attached to a top surface of PCB 480, over aperture 406 and at least a majority of the electronics disposed on PCB 480, thereby also serving as a physical cover thereover.

Respective first and second battery traces 488 may also be disposed on PCB 480 and are configured to directly or indirectly provide power from battery 216' to any and all electrical components of the sensor electronics module 8' that require battery power.

First transmit electrode 313 is illustrated as being disposed in and/or on PCB 480 to a first side of the sensor electronics 204' and second transmit electrode 314 is illustrated as being disposed in and/or on PCB 480 to a second side of the sensor electronics 204'. In some embodiments, this second side may be disposed in an opposite direction with respect to the sensor electronics 204' compared to the first side. In some embodiments, a bottom side of PCB 480 may comprise an adhesive layer disposed over at least the portions within or on which first and second transmit electrodes 313, 314 are disposed. Such an adhesive layer may be configured to allow for attachment of the sensor electronics module 8' to the skin or clothing of the host.

In some embodiments, a first portion of PCB 480 within or on which first transmit electrode 313 is disposed may be manufactured to have a first predetermined thickness configured to provide a first desired offset or insulated spacing between the first transmit electrode 313 and the tissue of the host, thereby providing a first amount of capacitive coupling between first transmit electrode 313 and the tissue of the host. A second portion of PCB 480 within or on which second transmit electrode 314 is disposed may have a second predetermined thickness configured to provide a different desired offset or insulated spacing between the second transmit electrode and the tissue of the host, thereby providing a second amount of capacitive coupling between second transmit electrode 314 and tissue of the host. In other embodiments, the second predetermined thickness over or under second transmit electrode 314 is greater than the first predetermined thickness over or under first transmit electrode 313, to provide a desired larger gap between second transmit electrode 314 and tissue of the host than there is between the first transmit electrode 313 and the tissue of the host as shown in FIGS. 2A and 2B.

Placing all circuitry on the single layer of adhesive-attached PCB 480 reduces the cost and thickness of the sensor electronics module 8' compared to some other designs, especially when a commercially available thin, flexible battery 216' is utilized (e.g., a printed battery about the size of a small gauze pad, as opposed to a larger coin-cell battery). Areas of PCB 480 in contact with the adhesive form a dielectric or insulative coupling mechanism for propagation of signals via, e.g., 21 MHz IEEE 802.15.6 HBC protocols or similar, to a suitably configured receiver.

In operation of this embodiment, sensor 10 generates an analog electrical signal indicative of a level of analyte (e.g., glucose) detected within the host. This analog electrical signal is provided from sensor 10 to sensor electronics which converts the analog signal to a digital signal suitable for communication through tissue of the host utilizing capacitive coupling-based HBC protocols. This digital signal is used to modulate a carrier signal and is then applied across first and second transmit electrodes 313, 314, which are disposed on the host's skin and/or tissue as previously described. When first and second receive electrodes 306, 307 of receiver 305 (such as display device 120', 140') (see, e.g., FIGS. 2A, 2B) are also properly disposed on the host's skin and/or tissue at a different location from sensor electronics module 8', provision of the modulated carrier signal across first and second electrodes 313, 314 causes HBC and signal propagation via direct path 330 and return path 340 (see, e.g., FIG. 2A).

Because HBC transmission through tissue of the host operates at a substantially lower frequency compared to other wireless protocols, such as BLE and WiFi and readily propagates through tissue of the host without substantial attenuation therethrough, and also because little or no signal processing, calibration and/or storage needs to occur in the sensor electronics, but instead may occur in one or more receivers (e.g., receiver 305), manufacture of sensor electronics module 8' can be less expensive in that fewer hardware components are required and those required components can be selected with lower cost due to the reduced processing and/or storage requirements. Moreover, less processing and more efficient wireless transmission utilizing HBC also presents a reduced power and/or current draw from battery 216', which allows battery 216' to be made smaller, cheaper and/or utilizing more convenient fabrication methodologies than can be used for battery 216 of FIG. 1B, such as on-substrate battery printing and/or adherence as previously described. All of these factors also provide for a sensor electronics module that may have more efficient operation and a lower profile than would otherwise be possible.

FIG. 3C is a top view of several hardware features of an advantageous physical implementation of sensor electronics module 8', according to some embodiments. In this embodiment, sensor electronics module 8' may comprise a PCB 480 that is flexible or has flexible portions comprising, for example polyimide or any other suitably flexible insulative material. Transmit electrodes 313, 314 may be disposed in and/or on flexible portions of PCB 480 on respective opposite sides of electrical traces and/or electronics as previously described in connection with sensor electronics module 8' of FIGS. 3A and 3B. The electronics located between the electrodes 313, 314 may be disposed on a flexible or rigid portion of PCB 480. This embodiment of sensor electronics module 8' may resemble a discreet flexible adhesive bandage that can be applied and removed in similar fashion and disposed of after use.

In the implementation of FIG. 3C, the analyte sensor 10 may be substantially or completely non-invasive and may be operably coupled to the sensor electronics module prior to placing the sensor electronics module on the host to begin a sensor session. Such a sensor design would make application of the sensor electronics module very user friendly to install, without requiring a transcutaneous sensor inserter as is common practice at this time. It could be as simple as applying a band-aid. Alternatively, a sensor 10 may first be inserted in a conventional manner attached to a base with conductive contacts thereon, onto which the sensor electronics module 8' is placed for operably connecting the sensor 10 with the sensor electronics module 8'.

Figure 3D:
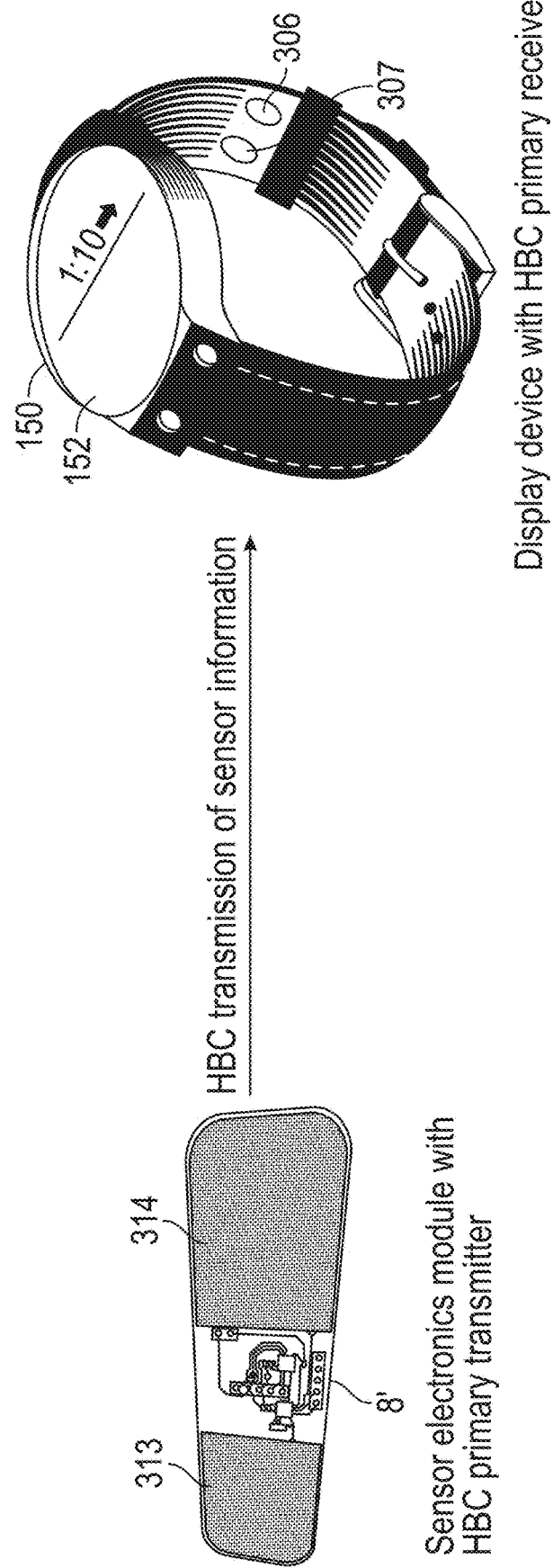
FIG. 3D illustrates a first analyte sensor system comprising a sensor electronics module and a display device configured for human body communication, according to some embodiments.

FIG. 3D illustrates a first analyte sensor system comprising a sensor electronics module and a display device configured for human body communication, according to some embodiments. FIG. 3D shows an implementation of the concepts described herein in the context of an analyte concentration monitoring system. This system comprises a sensor (not shown), a sensor electronics module 8' operably connected to the sensor containing a primary sensor information transmitter configured for HBC communication, and a display device 140' that comprises a primary sensor information receiver configured for HBC communication. A smartwatch 150 is an example display device for some embodiments because it includes a display 152 and also can include receive electrodes 306, 307 on the back of the watch body or on the inside of the band (as shown in FIG. 3D) to function as electrodes for HBC signal reception. In some embodiments, instead of electrodes 306, 307, the display device 150 may comprise an insulated high-Q magnetic antenna or pick-up coil to receive the HBC signal from the host tissue. A smartwatch can be an advantageous display device with a primary sensor information receiver configured for HBC communication because it is a device with internal data processing capabilities designed for extended contact with host tissue. However, as described in the embodiments below, the display device 150 can take a wide variety of different forms.

Accordingly, several example embodiments of an analyte sensor system that are also configured to communicate analyte data through tissue of the host utilizing HBC will now be described in connection with at least FIGS. 3E-3H.

Figure 3E:
FIG. 3E illustrates a second analyte sensor system comprising a sensor electronics module and a display device configured for human body communication, according to some embodiments.

FIG. 3E illustrates a second analyte sensor system comprising a sensor electronics module and a display device configured for human body communication, according to some embodiments. In FIG. 3E, the receiver is formed as a "smart-ring" 160, 160' instead of a smartwatch. The ring may include an alphanumeric display 162 or a simpler display mechanism such as LED lights 162' to present sensor information such as analyte concentrations to the host.

Figure 3F:
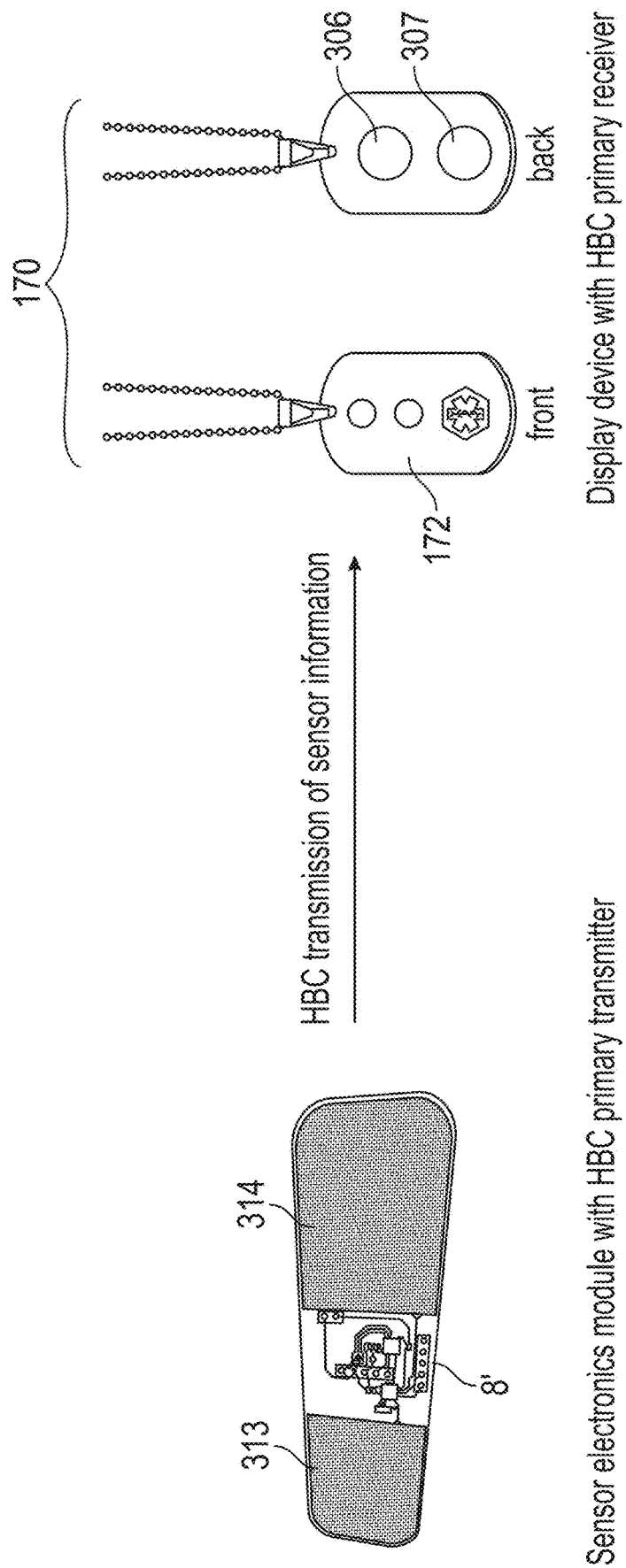
FIG. 3F illustrates a third analyte sensor system comprising a sensor electronics module and a display device configured for human body communication, according to some embodiments.

FIG. 3F illustrates a third analyte sensor system comprising a sensor electronics module and a display device configured for human body communication, according to some embodiments. In FIG. 3F, the display device is formed as a medical alert bracelet or necklace 170 with HBC contacts 306, 307 on one side, and LED display indicators 172 on the other.

Figure 3G:
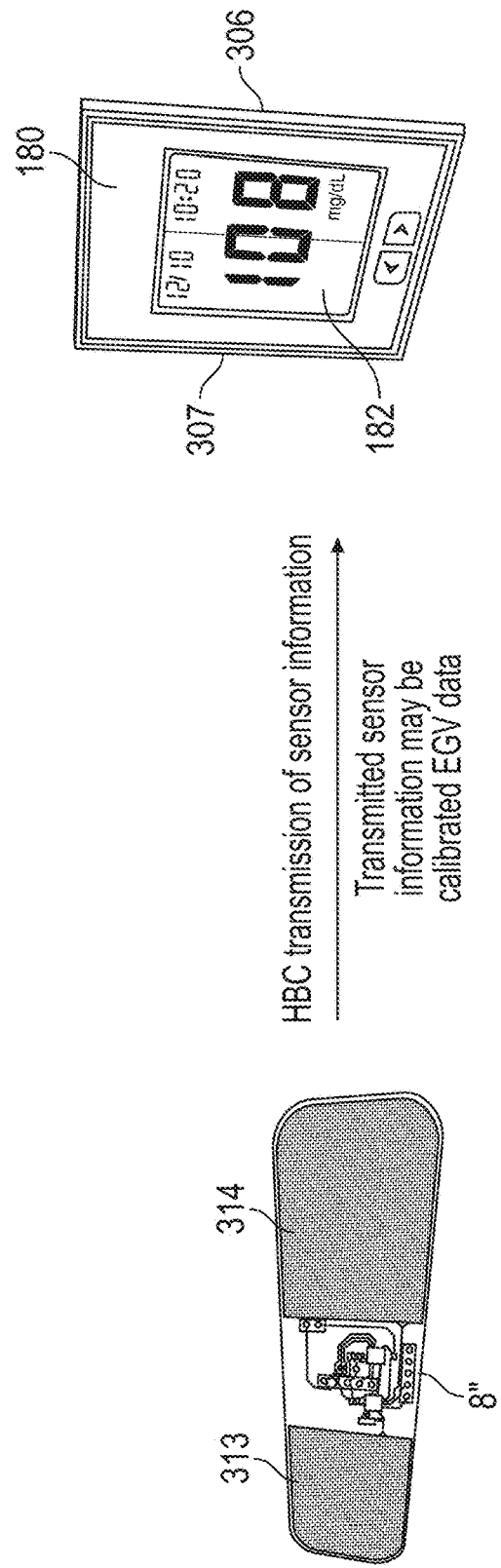
FIG. 3G illustrates a fourth analyte sensor system comprising a sensor electronics module and a display device configured for human body communication, according to some embodiments.

FIG. 3G illustrates a fourth analyte sensor system comprising a sensor electronics module and a display device configured for human body communication, according to some embodiments. In the embodiment shown in FIG. 3G, a display device 180 may be configured to act in a manner analogous to a single point glucose monitor when picked up by a host but which does not require a finger prick blood sample. In the system of FIG. 3G, the display device 180 has HBC receive electrodes 306, 307 on an external surface thereof. The sensor electronics module 8' may be configured to periodically (e.g., every 5 seconds, 10 seconds, 15 seconds, 20 seconds, or 30 seconds, etc.) transmit its most recently acquired sensor information with its transmit electrodes. The above numbers are merely example periodic times, other times are also possible. When the user picks up the display device 180, the receive electrodes 306, 307 on the external surface of the display device 180 come into contact with the host's skin. The display device 180 then listens for a transmission from the sensor electronics module 8', which should occur within 10 seconds of picking up the display device 180. After receiving the transmitted sensor information, the display device 180 displays the received sensor information or information derived therefrom (e.g., a current EGV data point) on the display 182.

The display device 180 of FIG. 3G may be implemented in a variety of ways. The specific illustrated example is a dedicated device similar in form factor to a conventional single point glucose monitor that would receive a test strip blood sample and output a glucose value read from the strip. In another embodiment, a USB dongle could have HBC electrodes on an external surface thereof. The USB dongle could be plugged into an I/O port on a smartphone, tablet, PC, or other display/computing device. The USB dongle may receive analyte data communications via HBC through the host's fingers contact with the receive electrodes and deliver them to the computing device Appropriate software such as a downloadable smartphone app may receive the data from the dongle for display thereon.

Such embodiments may allow for on-demand acquisition of estimated analyte values without user-specific pairing between the sensor electronics module 8" and display device 180. At least one reason user-specific pairing is not required is that capacitively coupled or galvanically coupled HBC transmitters and receivers can only communicate with one another via HBC through the tissue of the host and, so, require direct skin/tissue contact of the transmit and receive electrodes (either through insulated contacts or pickup coils in the case of capacitively coupled devices, or through conductive contacts in the case of galvanically coupled devices), which provides a measure of privacy and security in and of itself.

As illustrated in FIG. 3G, and as previously described, sensor electronics module 8" is configured to communicate with display device 180 through tissue of a host utilizing HBC. In some embodiments of the system of FIG. 3G, the sensor electronics module 8" may be configured to periodically or continually modulate and transmit data packets through tissue of the host utilizing any suitable frequency (e.g., 20 MHz). In some embodiments in connection with FIG. 3G the sensor electronics module 8" is configured to perform calibration, processing and estimation of glucose values utilizing an internal processor, to store one or more of sensor data and estimated analyte concentration data utilizing an internal memory, and to continually or periodically transmit the data or information derived therefrom via HBC through tissue of the host. Accordingly, in some embodiments, the display device may receive a series of analyte data points, possibly with associated time stamps, and may therefore be able to display a graph output of analyte concentration data similar to a CGM device. It will be appreciated that in some embodiments, sensor electronics module 8" measures and transmits raw sensor data or minimally processed sensor data (e.g., A-D conversion, filtered) to the display device 180. In such embodiments, display device 180 will further process the received data from the sensor electronics module 8″ to provide estimated glucose values or any other meaningful values suitable for a user to understand.

In some embodiments, the display device 180 may be configured not to store estimated glucose values or other analyte data communicated through tissue 50 by the sensor electronics module 8″ but to display a single, most recently generated estimated glucose value when held by the host (e.g., in the host's hand). For example, sensor electronics module 8″ may be configured to continuously or periodically transmit data packets comprising estimated analyte concentration values through tissue of the host. The host picking up and holding the display device 180 completes an HBC circuit between sensor electronics module 8″ and display device 180 through tissue, as previously illustrated in connection with at least FIGS. 2A, 2B, and 3A, and the data packet with the estimated analyte concentration value is received by the display device 180 for presentation to the host on display 182.

In some embodiments, display device 180 is configured to display a countdown or other animation on its display while waiting to decode a next estimated glucose value transmission from sensor electronics module 8″ in order to, for example, mimic the integration process of a handheld blood glucose meter. In some embodiments, display device 180 may be configured to wake from a low-power sleep mode based on sensing that the display device 180 has been touched and/or picked up by the host, for example utilizing established capacitive sensing technology.

Some embodiments of the system illustrated in FIG. 3G allow sharing of system components within a household or clinic, for example, since all sensor electronics modules 8″ may be configured to communicate with all display devices 180 without a pairing procedure and, at least in these embodiments, estimated glucose values may not be stored in the display devices 180.

As previously described, in some embodiments, replacing BLE communication with HBC communication allows both sensor electronics module 8′, 8″ and display device 150, 160, 170, 180 to omit or turn off BLE radio modules, which reduces peak and continuous power demand compared to BLE-based transmitters. Where BLE radio modules are omitted, omission of BLE antennas, which require a minimum separation from the body of the host to maintain communication performance, also allows a smaller minimum height of the wearables. All of this allows for discreet, ultra-low-profile and ultra-low-cost sensor electronics modules that further enjoy lower power draw and increased battery lifetimes.

Figure 3H:
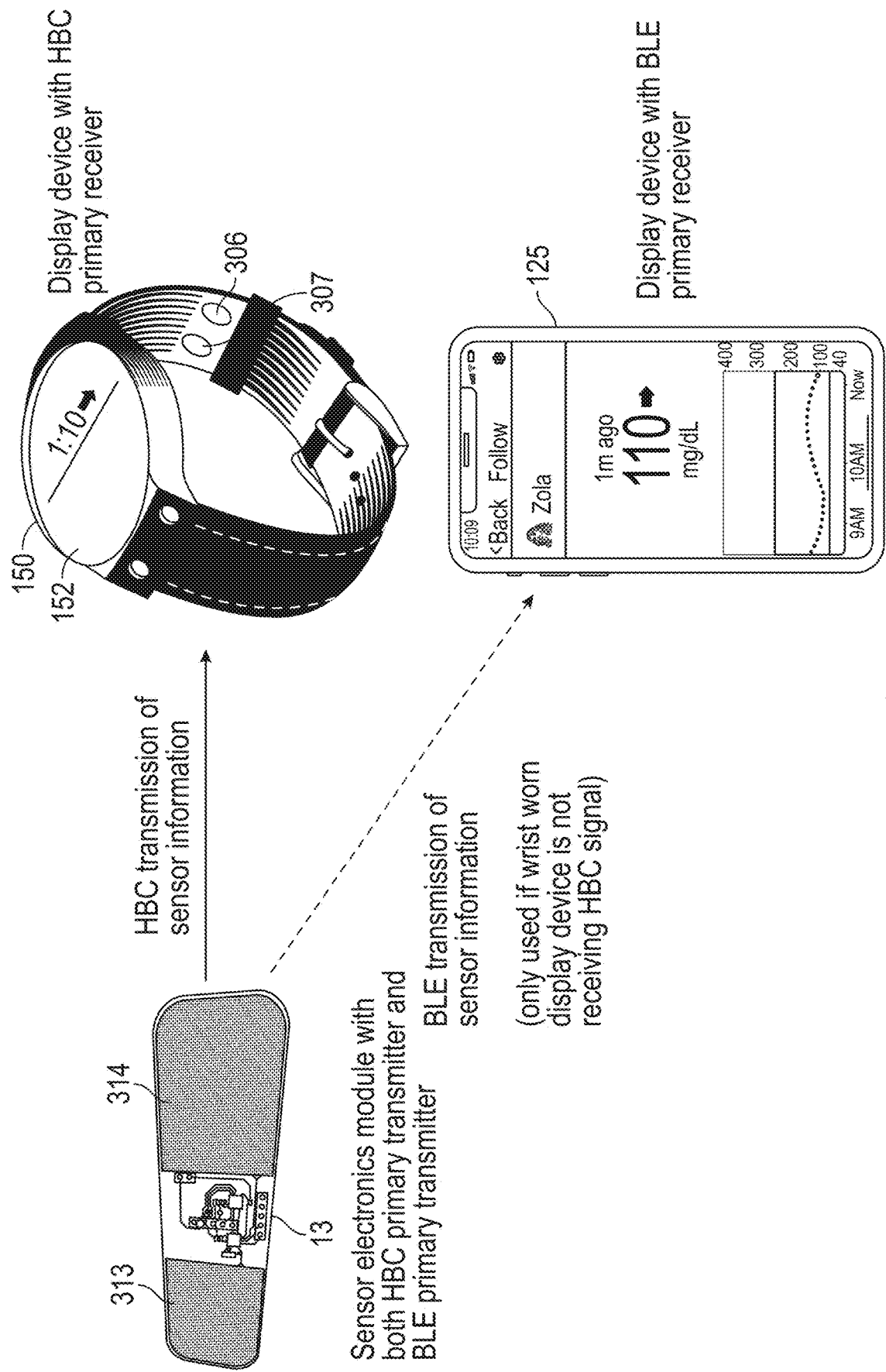
FIG. 3H illustrates a fifth analyte sensor system comprising a sensor electronics module and a display device configured for human body communication, according to some embodiments.

FIG. 3H illustrates a fifth analyte sensor system comprising a sensor electronics module and a display device configured for human body communication, according to some embodiments. Other example embodiments of an analyte sensor system are described in connection with FIG. 3H. In some embodiments, compatible with both capacitively coupled and galvanically coupled HBC embodiments described herein, a sensor electronics module 8‴ may, in addition to comprising first primary transmitter circuitry for transmitting data through tissue of the host via HBC to a first display device 150 such as a smartwatch as previously described, may also comprise second primary transmitter circuitry (not shown in the Figures) configured to communicate with another display device 125 utilizing a second communication protocol that does not utilize the tissue of the host as a primary transmission medium (e.g., BLE, WiFi, 4G LTE). The second higher power primary transmitter circuitry may be used only if the first display device 150 is not receiving an HBC signal from sensor electronics module 8‴ through tissue, as determined, for example, by an absence of HBC ACK messages from the display device 150 back to the sensor electronics module 8‴.

In some such embodiments, the sensor electronics module 8‴ is configured to maintain the second primary transmitter circuitry in a powered-down or low-power sleep state as long as a live HBC link between the sensor electronics module 8‴ and the first display device 150 is maintained. However, in such embodiments, the sensor electronics module 8‴ may be configured to determine that the display device 150 is not receiving an HBC signal from sensor electronics module 8‴ through tissue. Based on such a determination, sensor electronics module 8‴ may be configured to turn on, power up, or cause the second wireless communication module to exit a low-power, sleep mode and communicate one or more analyte data signals (e.g., analog, raw digital, partially or wholly processed analyte data, estimated glucose values, or alerts) to another display device 125 utilizing the second communication protocol (e.g., BLE, WiFi, 4G LTE). In this way, many of the benefits of utilizing HBC over other, more power-intensive and/or higher-frequency wireless communication protocols can be realized while also providing alternative routes for communicating analyte data when such HBC protocols fail or are otherwise unavailable or unsuitable.

A similar technique can be used in the specific context of swimming or bathing. Swimming and/or being submerged in water can bring unique challenges to users of analyte sensor systems. While swimming, a host's sensor electronics module 8″ is inevitably submerged at least some of the time. Analyte monitoring systems that use transmitters and receivers that rely on communication protocols such as BLE and WiFi are not capable of communicating in water, since 2.4 GHz radio waves do not propagate significantly through water. Consequently, parents of pediatric patients must remove them from a swimming pool and adult patients must exit the pool to periodically consult their receivers 140, 120 (FIGS. 1A and 1B). While this is less inconvenient than the use of recurrent finger sticks, such requirements can still present considerable burdens for users of such analyte sensor systems.

In contrast, HBC through the tissue of the host, for example at approximately 20 MHz-approximately 21 MHz or, where lower frequencies are more desirable, approximately 10 MHz, are able to traverse the body tissues of a submerged host to a location of the body that is easily visible to the host or a caretaker of the host.

Accordingly, in some embodiments, sensor electronics module 8‴ and display device 150 may be substantially waterproof. The display device 150 may comprise at least one light emitting source (e.g., a light emitting diode (LED)) and may be configured to cause LED to emit or flash one of a plurality of colors indicative of an estimated analyte concentration value received from the sensor electronics module via HBC through tissue 50 of the host. For example, display device 150 may be configured to cause an LED to emit or flash red light when the received estimated analyte concentration value is outside a safe range, yellow light when the received estimated analyte concentration value is within a predetermined range near an edge or outside boundary of such a safe range, and green light when the received estimated analyte concentration value is sufficiently within such a safe range. It will be appreciated that the display device 150 can be configured to cause LEDs to emit any pattern and/or color(s) of light indicative of different levels of estimated analyte concentration values. In this way, either the host, him or herself, or a caregiver of the host can view LEDs on the display device 150 while in the water or from a distance outside the water and determine, at a glance, whether the host's estimated analyte concentration value is sufficiently within a safe range, nearing the edge of a safe range, or outside a safe range. In some embodiments, the display device is further, or alternatively, configured to cause display LEDs to emit a unique pattern and/or color(s) of light to indicate if and when an HBC communication session between the sensor electronics module 8''' and display device 150 is no longer live, to thereby provide similar notification to the host or the host's caregiver of such a condition. While display device 150 is illustrated as a wristband and/or smartwatch that may be waterproof, the present disclosure is not so limited and the display device 150 can be any suitable wearable device or integrated into an article of clothing, for example, integrated into a swim cap.

Figure 4A:
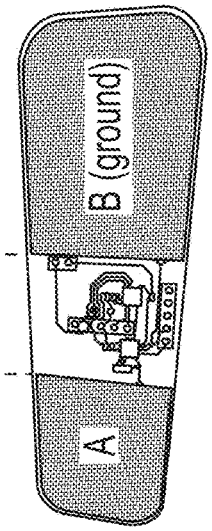
FIG. 4A is a table of a plurality of different configurations of insulated transmission electrodes that may be utilized for human body communication, according to some embodiments.
Figure 4B:
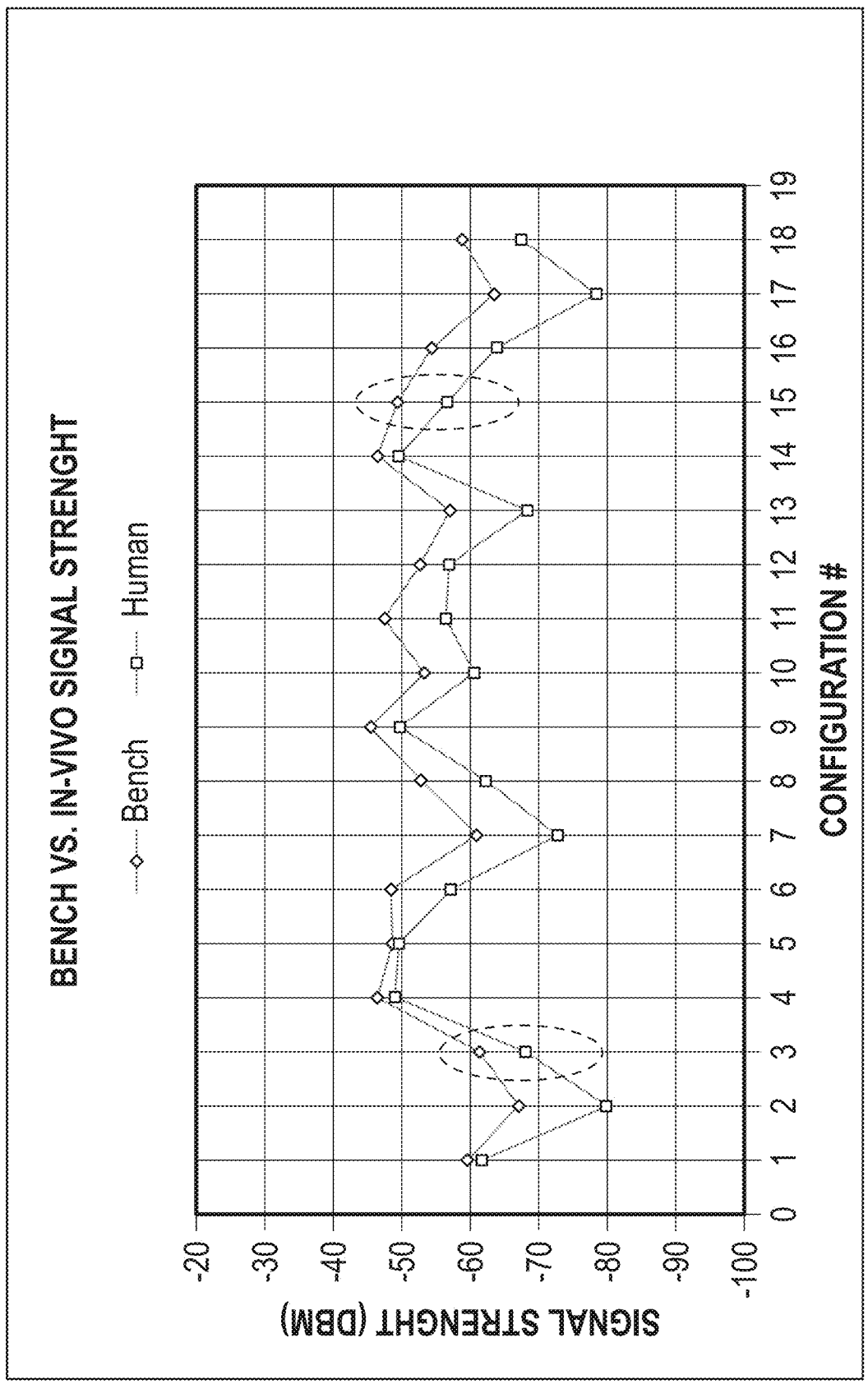
FIG. 4B is a graph showing relative received signal strength at a human body communication receiver when the transmitter electrodes have the configurations tabulated in the table of FIG. 4A.

FIG. 4A is a table of a plurality of different configurations of insulated transmission electrodes that may be utilized for human body communication, according to some embodiments. FIG. 4B is a graph showing relative received signal strength at a human body communication receiver when the transmitter electrodes have the configurations tabulated in the table of FIG. 4A. It has been surprisingly found that received signal strength is improved if the transmit electrode 313 having a higher capacitive coupling to the tissue has a greater surface area than the transmit electrode 314 with a smaller capacitive coupling to the tissue. This is illustrated in FIGS. 4A and 4B. FIG. 4A shows eighteen different configurations of transmit electrodes and driver circuits, varying by applied carrier frequency, electrode area for each of the transmit electrodes 313 and 314 and distance between the electrodes 313 and 314. FIG. 4B shows the signal strength results obtained with the different configurations from the table of FIG. 4A.

Comparing the results of configuration 3 (circled in black) with configuration 15 (circled in red), it can be seen that for all other parameters equal, larger electrode 313 and smaller electrode 314 has better performance than the other way around. So for a given total electrode area between both electrodes, allocating more area to electrode 313 is advantageous.

Figure 5A:
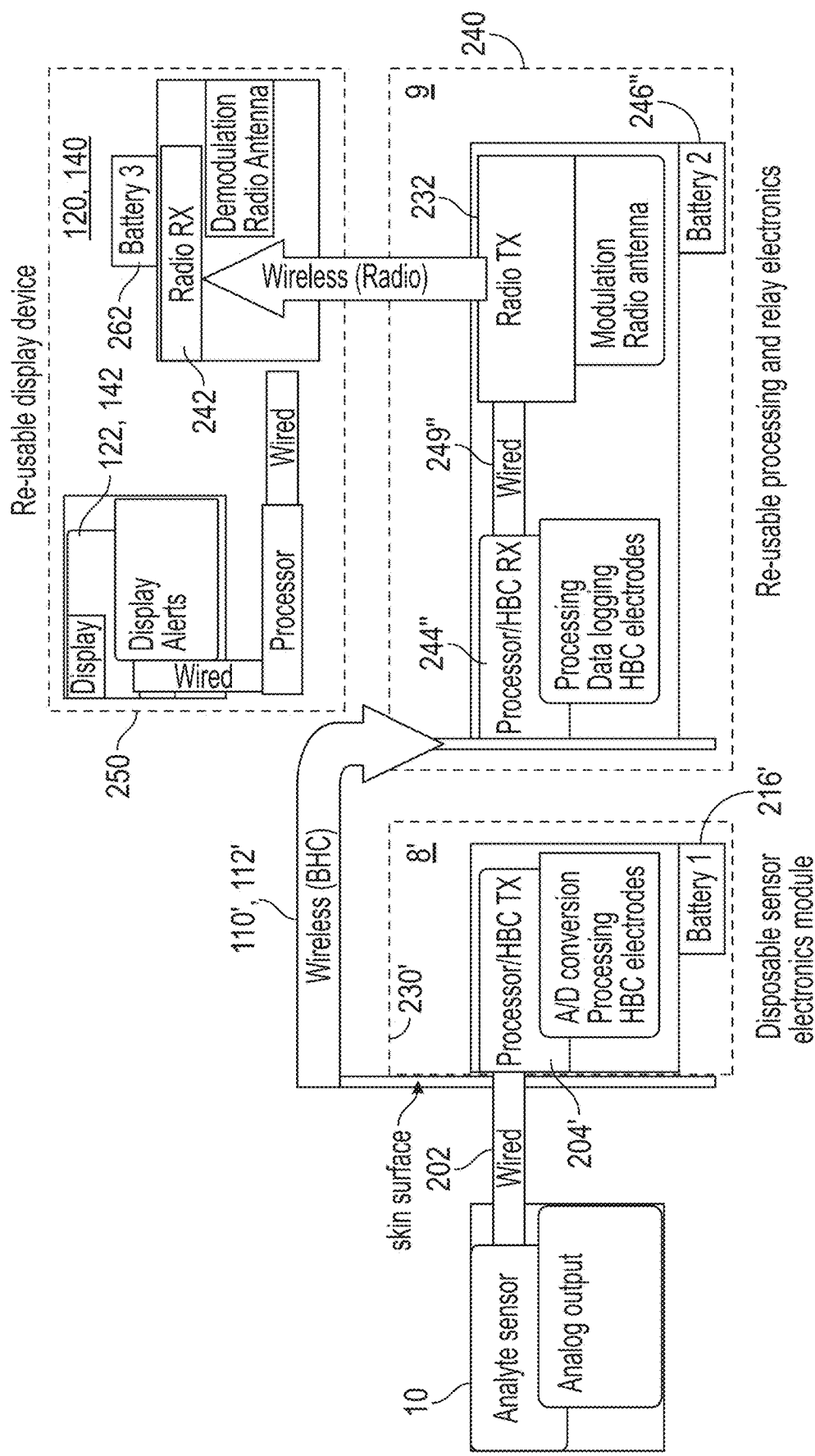
FIG. 5A is a schematic block diagram of another HBC analyte sensor system, according to some embodiments.

FIG. 5A is a schematic block diagram of another HBC analyte sensor system, according to some embodiments. FIGS. 5B-5E respectively illustrate sixth to ninth analyte sensor systems each comprising a sensor electronics module, a display device, and other components configured for human body communication, according to some embodiments. In some embodiments, as shown in FIGS. 5A through 5D, a relay module 9 may be utilized that functions as a primary sensor information receiver. The primary sensor information receiver may comprise one or more wireless communication modules and/or transceivers configured to communicate utilizing a second communication protocol different from HBC, e.g., that does not utilize the tissue of the host as a primary transmission medium, for example BLE, WiFi, 4G LTE or any other similar, suitable wireless communication protocol so as to function as a secondary sensor information transmitter. In these embodiments, primary sensor information receiver 9 may receive sensor information from sensor electronics module 8' via a first HBC channel and/or communication session and also provide a communication bridge over a second channel between relay module 9 and another peripheral device 120, 140 utilizing the second communication protocol (e.g., BLE, WiFi, 4G LTE) to periodically relay sensor information to peripheral device 120, 140. In some such embodiments, some or all of the calibration and/or processing of the sensor information transmitted from sensor electronics module 8' to relay module 9 can be performed by the relay module 9 before relaying the original and/or processed form of the sensor information to display device 120. In other embodiments, some or all of the calibration and/or processing of the sensor information transmitted to relay module 9 can, instead, be performed by display device 120, while the relay module 9 is configured to simply relay the original sensor information received from primary transmitter 312 over the first communication channel via HBC, to display device 120, 140 via the second communication protocol (e.g., BLE, WiFi, 4G LTE or any other cellular communication protocol).

In embodiments shown in FIGS. 5A through 5E, at least one relay module 9 functions as a primary sensor information receiver and also functions as a secondary sensor information transmitter, according to the respective definitions established herein. Accordingly, display device 120 shown in FIGS. 5B, 5C, 5D, and 5E are configured to function as secondary sensor information receivers of analyte data, according to the definition established herein.

Figure 5B:
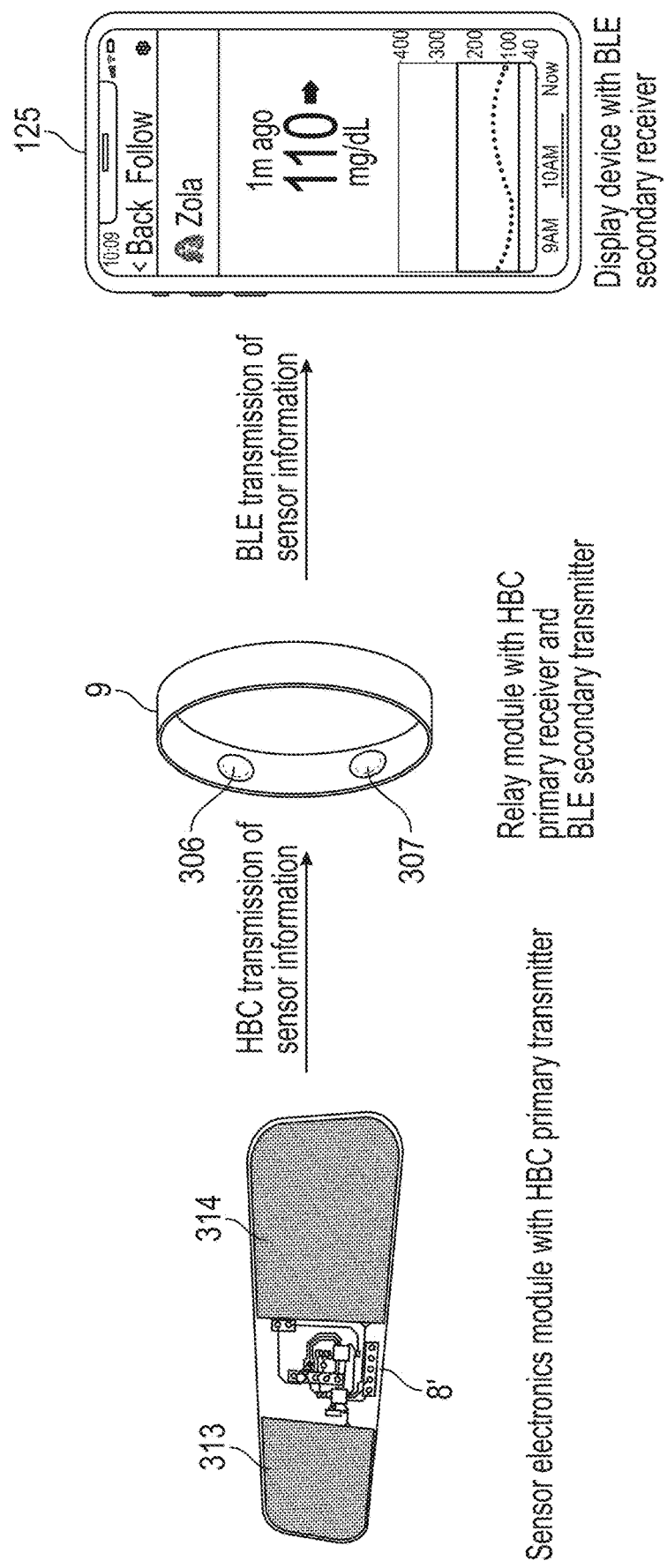
FIG. 5B illustrates a sixth analyte sensor system comprising a sensor electronics module, a display device, and other components configured for human body communication, according to some embodiments.
Figure 5C:
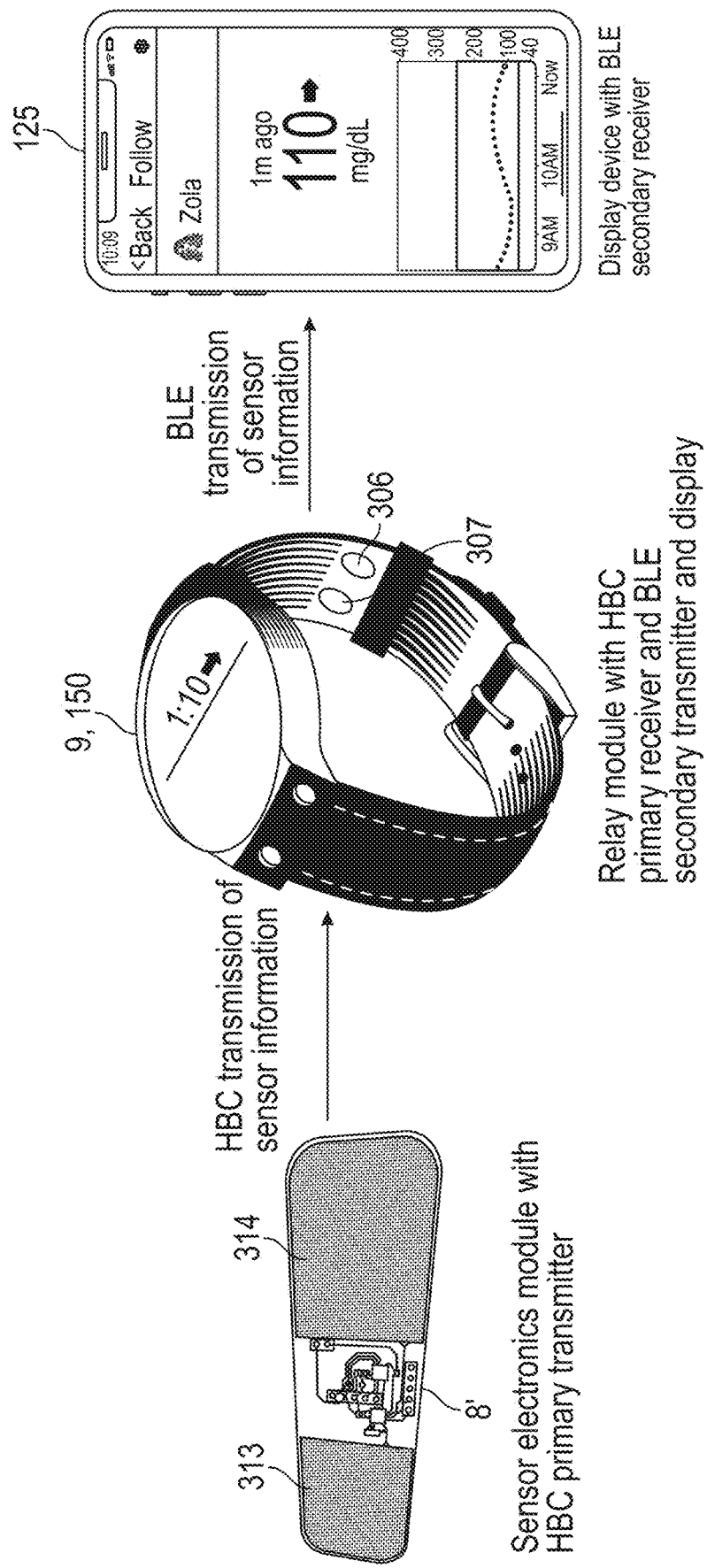
FIG. 5C illustrates a seventh analyte sensor system comprising a sensor electronics module, a display device, and other components configured for human body communication, according to some embodiments.

In FIG. 5B, a wristband is used as a relay module 9. In FIG. 5C, a smartwatch is used as both a relay module 9 and a display device 140'.

Figure 5D:
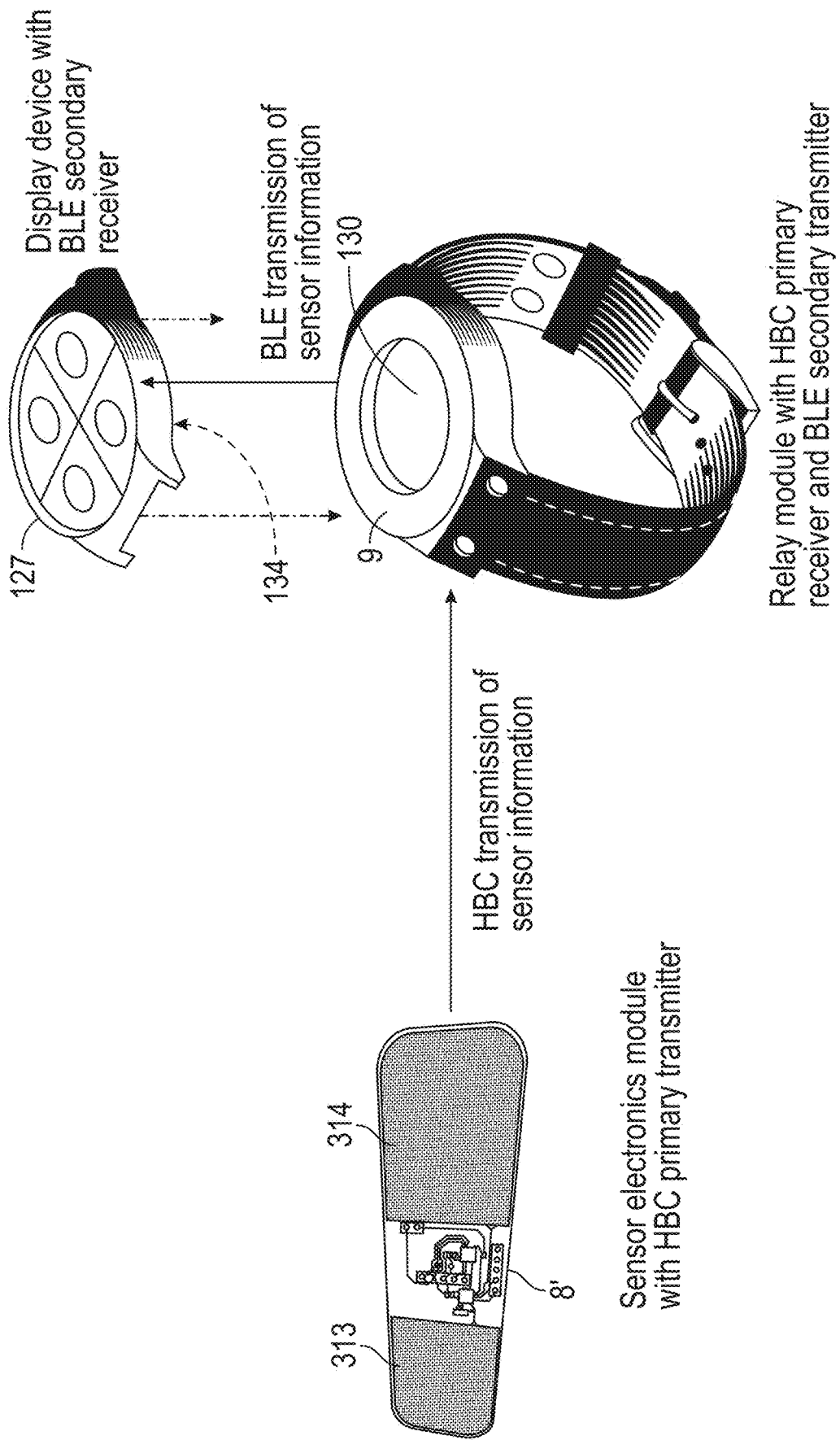
FIG. 5D illustrates an eighth analyte sensor system comprising a sensor electronics module and a display device configured for human body communication, according to some embodiments.
Figure 5E:
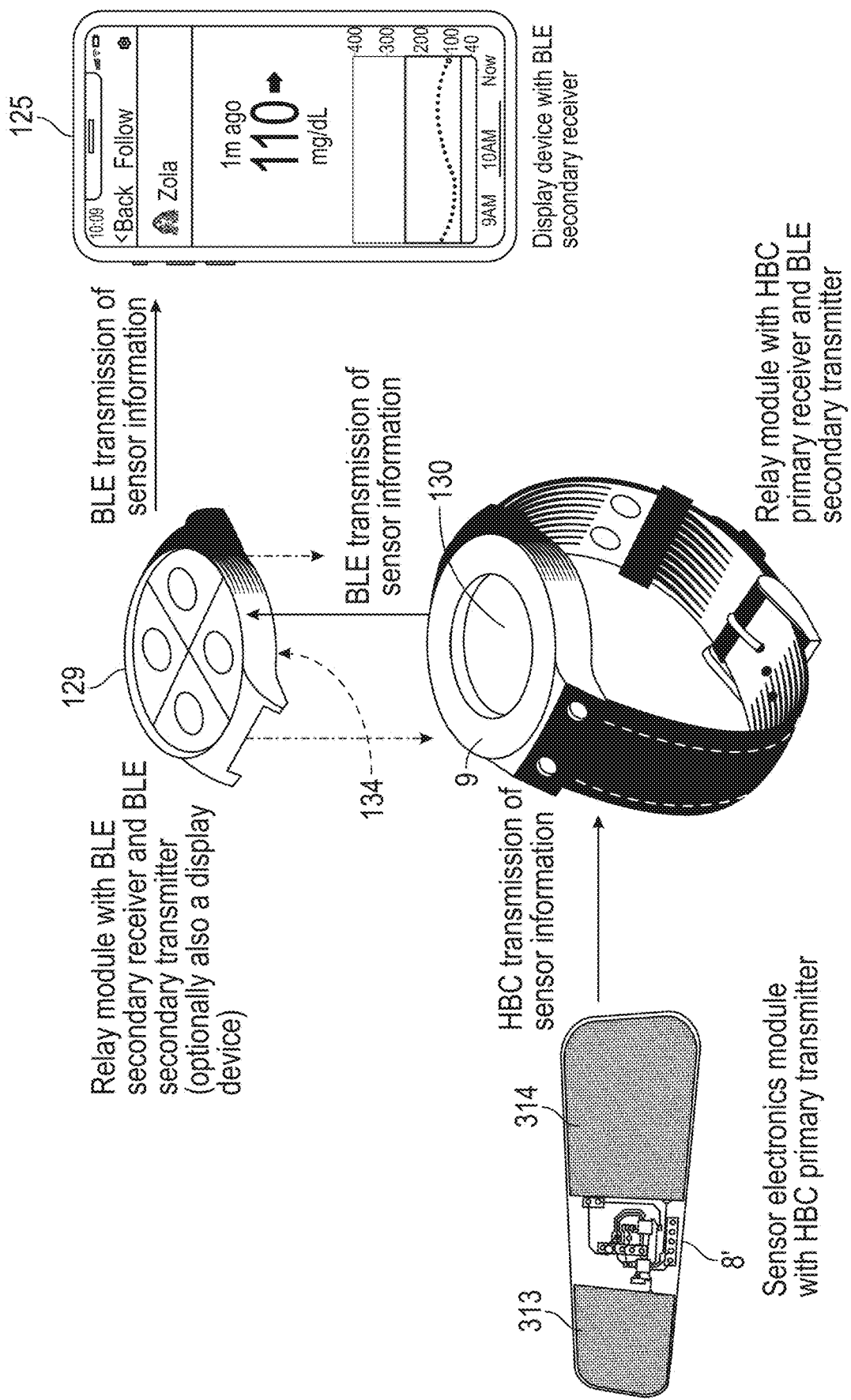
FIG. 5E illustrates a ninth analyte sensor system comprising a sensor electronics module and a display device configured for human body communication, according to some embodiments.

In FIG. 5D, a relay device 9 and display device 127 are separate devices but are connectable, wherein a wrist band forming the relay device 9 includes receive electrodes. A display device 127 can be attached to the wristband. The wristband may use HBC to receive sensor information from the sensor electronics module 8' and may transmit that sensor information to the display component by a different wireless communication protocol such as BLE. The wristband may include a charging coil for wireless charging the wristband at the same time that the display component is charged in a conventional manner for smartwatches. An opening 130 may be provided in the mounting hardware for the display component to allow contacts 134 (not shown) mounted on the bottom of the display device for other bio-signal monitoring purposes that are provided with some smartwatches to contact the user's skin through the middle of the wristband that contains the charging coil. FIG. 5E is similar to FIG. 5D except the wrist mounted display device functions as a relay device 9 to another display device 125.

Figure 6A:
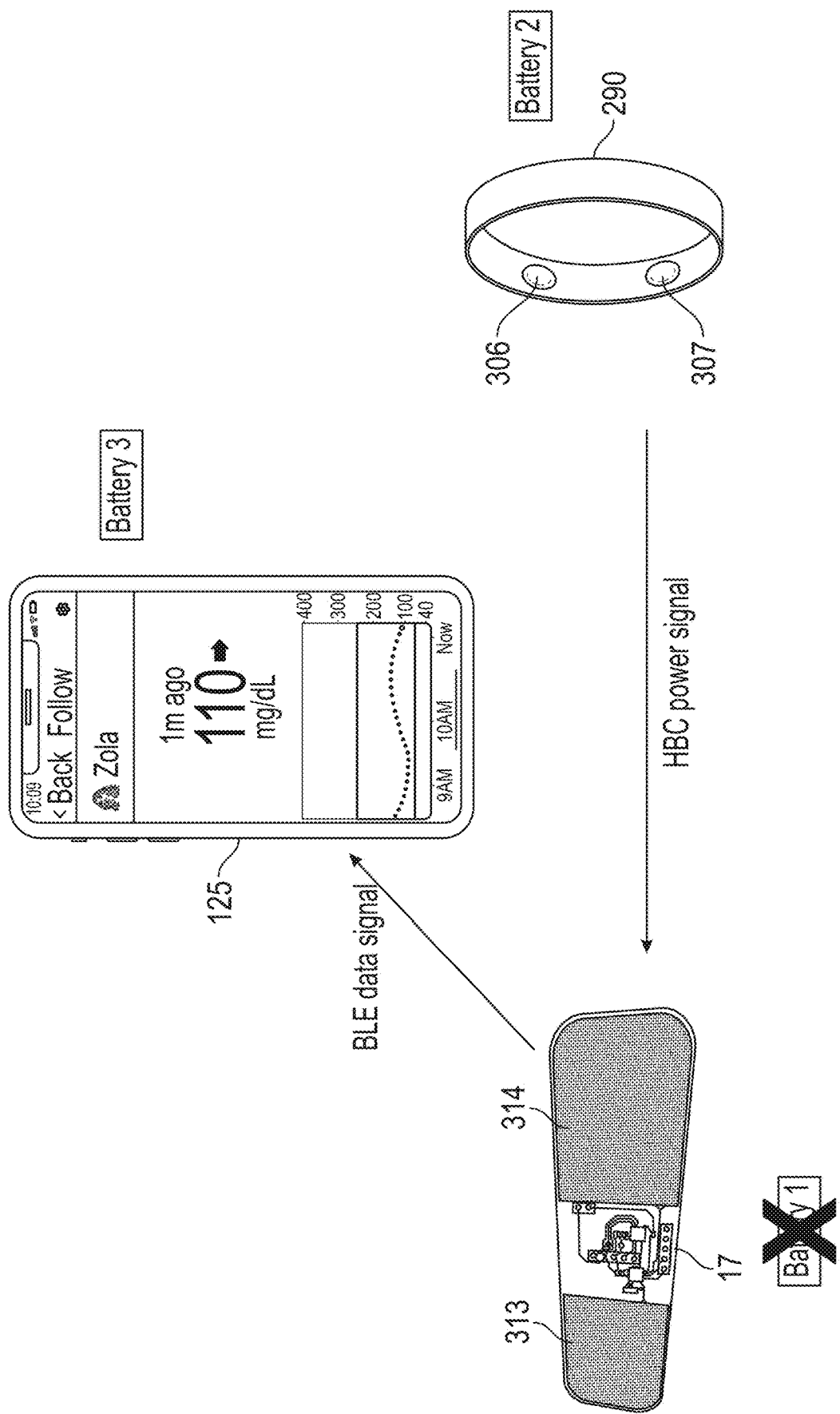
FIG. 6A illustrates a tenth analyte sensor system comprising a sensor electronics module and a display device configured for human body communication, according to some embodiments.

FIG. 6A illustrates a tenth analyte sensor system comprising a sensor electronics module and a display device configured for human body communication, according to some embodiments. FIGS. 6B-6F respectively illustrate eleventh to fifteenth analyte sensor systems each comprising a sensor electronics module and a display device configured for human body communication, according to some embodiments. Yet further example embodiments of analyte sensor systems configured to communicate through tissue of a host using HBC and harvest power wirelessly communicated through the tissue of the host will now be described in connection with FIGS. 6A-6C.

In some embodiments, instead of utilizing an on-board battery, one or more of a primary sensor information transmitter and primary sensor information receiver of the analyte sensor system can instead include a capacitor for storing energy. Energy for storage in the capacitor can be harvested from signals wirelessly transmitted through tissue of the host by another device of the analyte sensor system. Such an energy harvesting component of the analyte sensor system can then be powered by the charged capacitor. The absence of an onboard chemical-storage battery cell makes such analyte sensor systems cheaper, lower profile, and more environmentally friendly. Whereas human body tissue substantially blocks energy radiated in the GHz range, human body tissue is a good conductor of energy radiated in the MHz range. Accordingly, RF energy radiated through the tissue of the host between a primary sensor information transmitter and primary sensor information receiver, and at similar or the same frequencies as HBC protocols but for power transfer, easily propagates the one to two meter distance between primary transmitter and primary receiver across the host's tissues and, further, doesn't radiate significantly off the host's body.

Figure 6B:
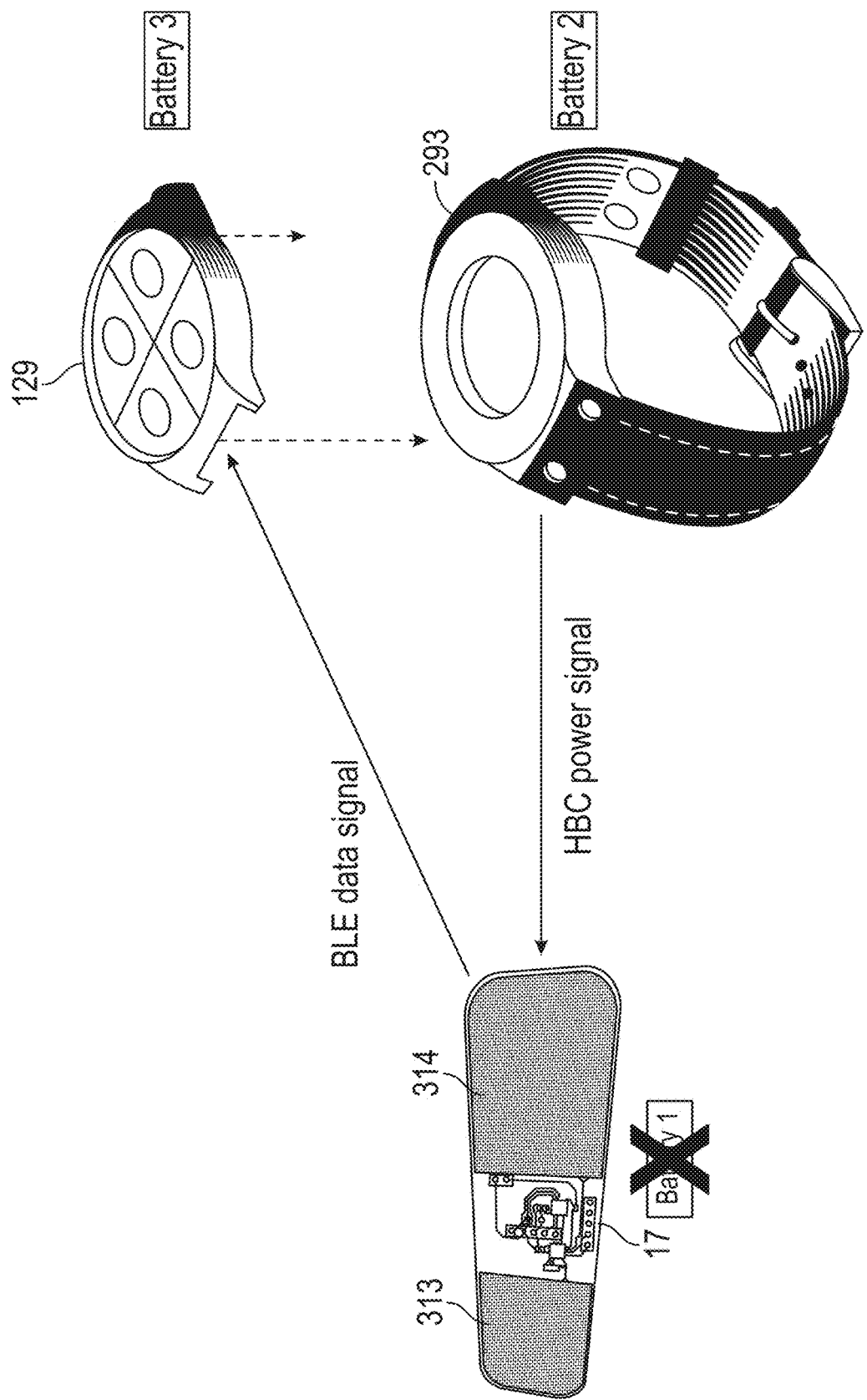
FIG. 6B illustrates an eleventh analyte sensor system comprising a sensor electronics module and a display device configured for human body communication, according to some embodiments.
Figure 6C:
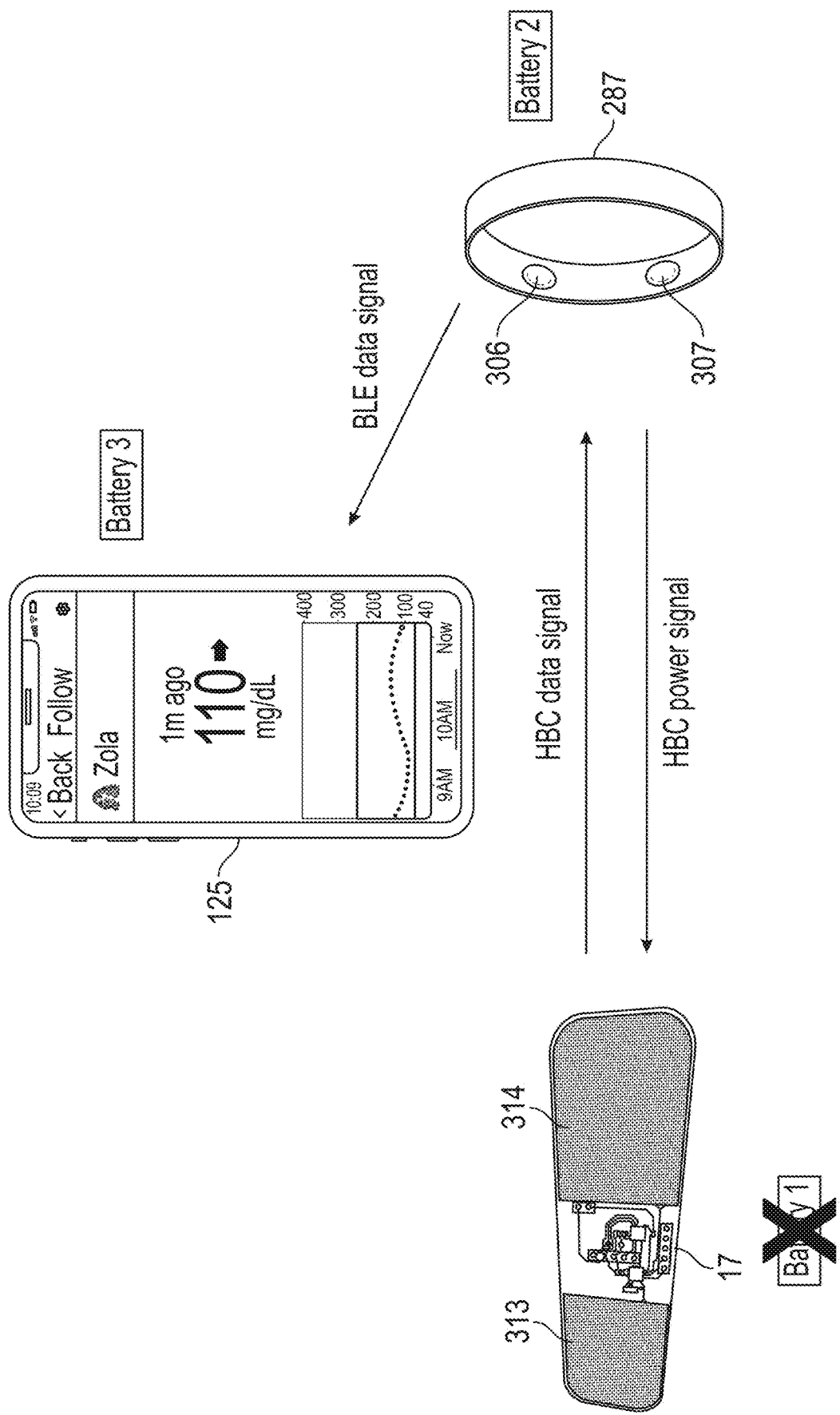
FIG. 6C illustrates a twelfth analyte sensor system comprising a sensor electronics module and a display device configured for human body communication, according to some embodiments.
Figure 6D:
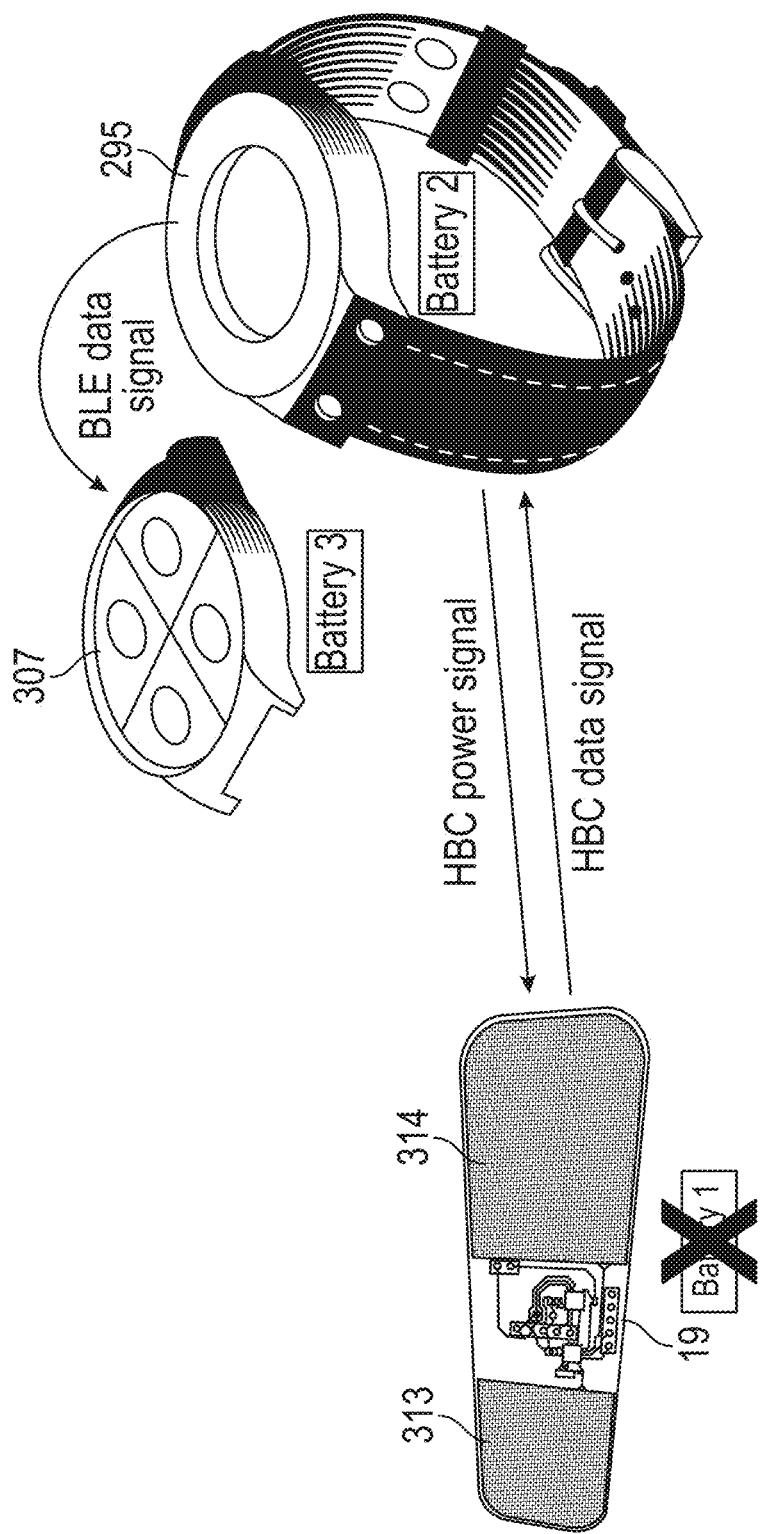
FIG. 6D illustrates a thirteenth analyte sensor system comprising a sensor electronics module and a display device configured for human body communication, according to some embodiments.
Figure 6E:
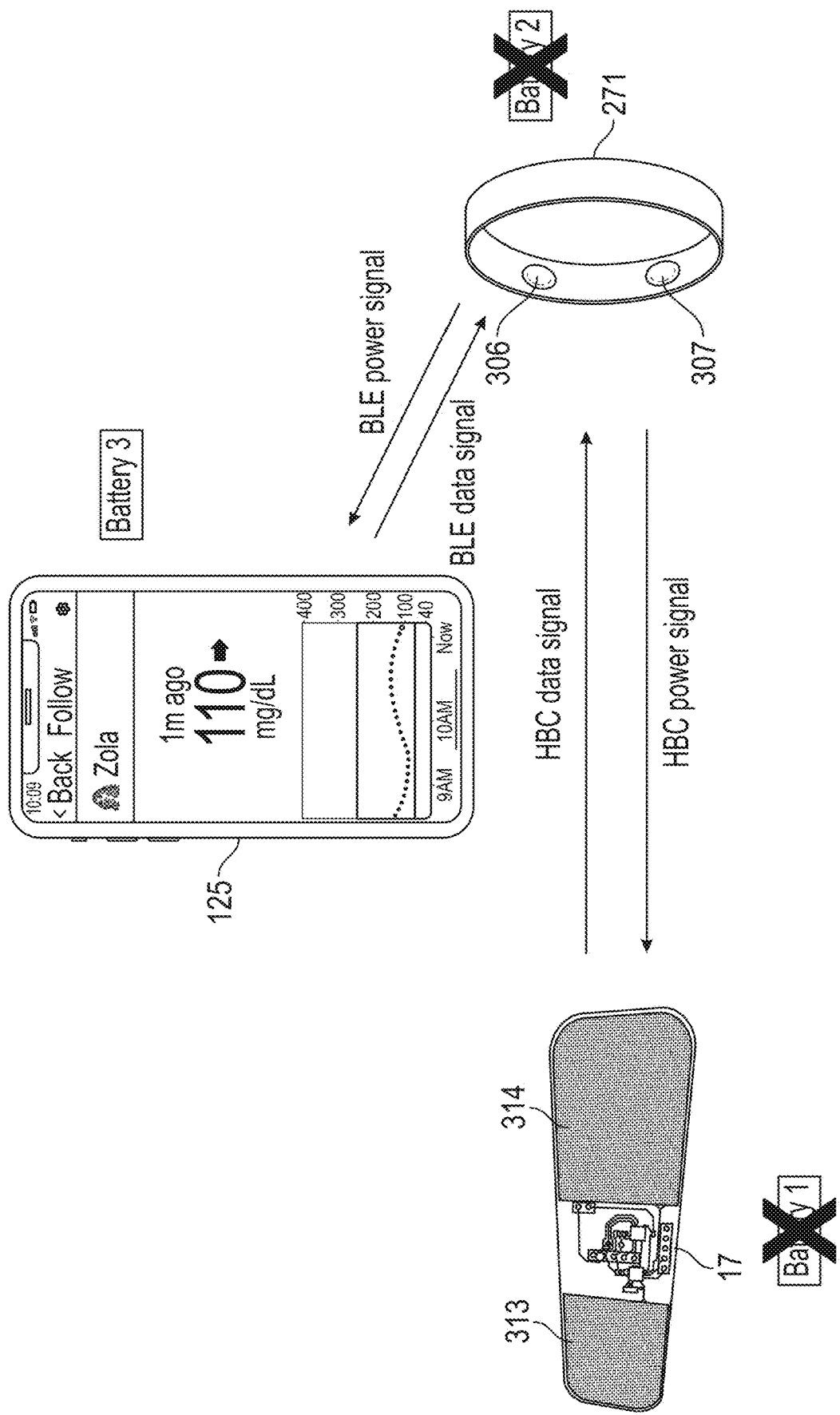
FIG. 6E illustrates a fourteenth analyte sensor system comprising a sensor unit and a display device configured for human body communication, according to some embodiments.
Figure 6F:
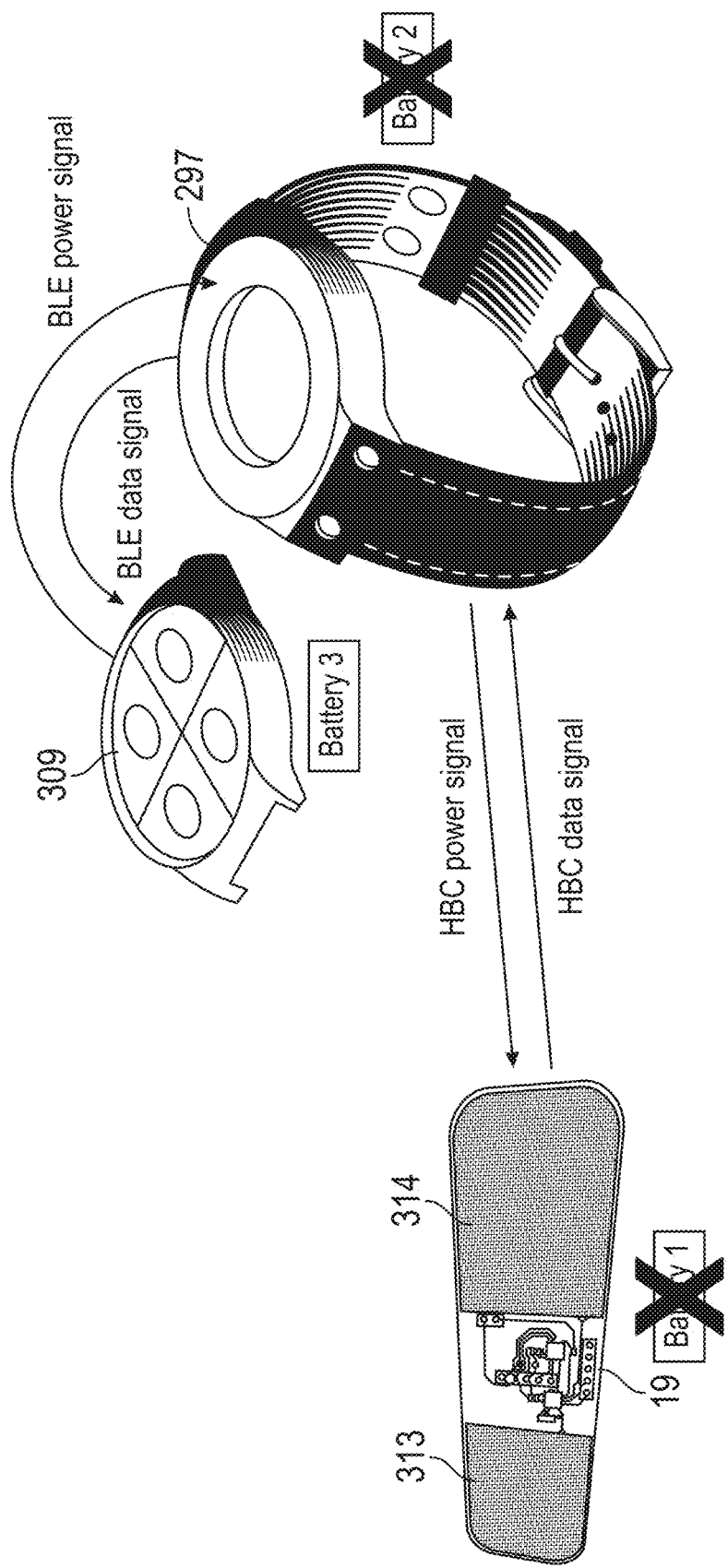
FIG. 6F illustrates a fifteenth analyte sensor system comprising a sensor unit and a display device configured for human body communication, according to some embodiments.

In some embodiments such as the embodiment illustrated in FIG. 6A, an analyte sensor system includes a battery containing wrist band 290 that functions as a power supply for HBC signal energy that can be harvested by the sensor electronics module 17. In this embodiment, the disposable sensor electronics module 17 needs no battery as illustrated in FIG. 6A by the X over Battery 1 (designated 216' in FIG. 5A). Instead, a battery in the wrist band, Battery 2 (designated 246" in FIG. 5A, which may or may not be rechargeable), supplies the power for the sensor electronics module 17 indirectly. The sensor electronics module 17 may include a BLE primary transmitter to transmit sensor information to a display device 125. In FIG. 6B, the wrist band is configured as a watch band 293 that functions as a power source. A smartwatch body 129 may function as a display device receiving sensor information from the sensor electronics module 17 via BLE communication from the sensor electronics module in this example. In FIG. 6C, a wrist band 287 functions as both a power source and a relay module. In, FIG. 6D, a watch band 295 functions as both a power source and a relay module. In FIG. 6E, a wrist band 271 receives power from a smart phone 125, and therefore needs no battery. In this embodiment, the wrist band 271 functions as a power transmitter, power receiver, and relay module. In FIG. 6F, a watch band 297 receives power from a watch body 309, and therefore needs no battery as well. While the HBC power transmitter is illustrated in FIGS. 6A-6F as being incorporated into a wearable wristband, the present disclosure contemplates such a power transmitter being integrated into any suitable device, including but not limited to a key fob or pendant.

Figure 7A:
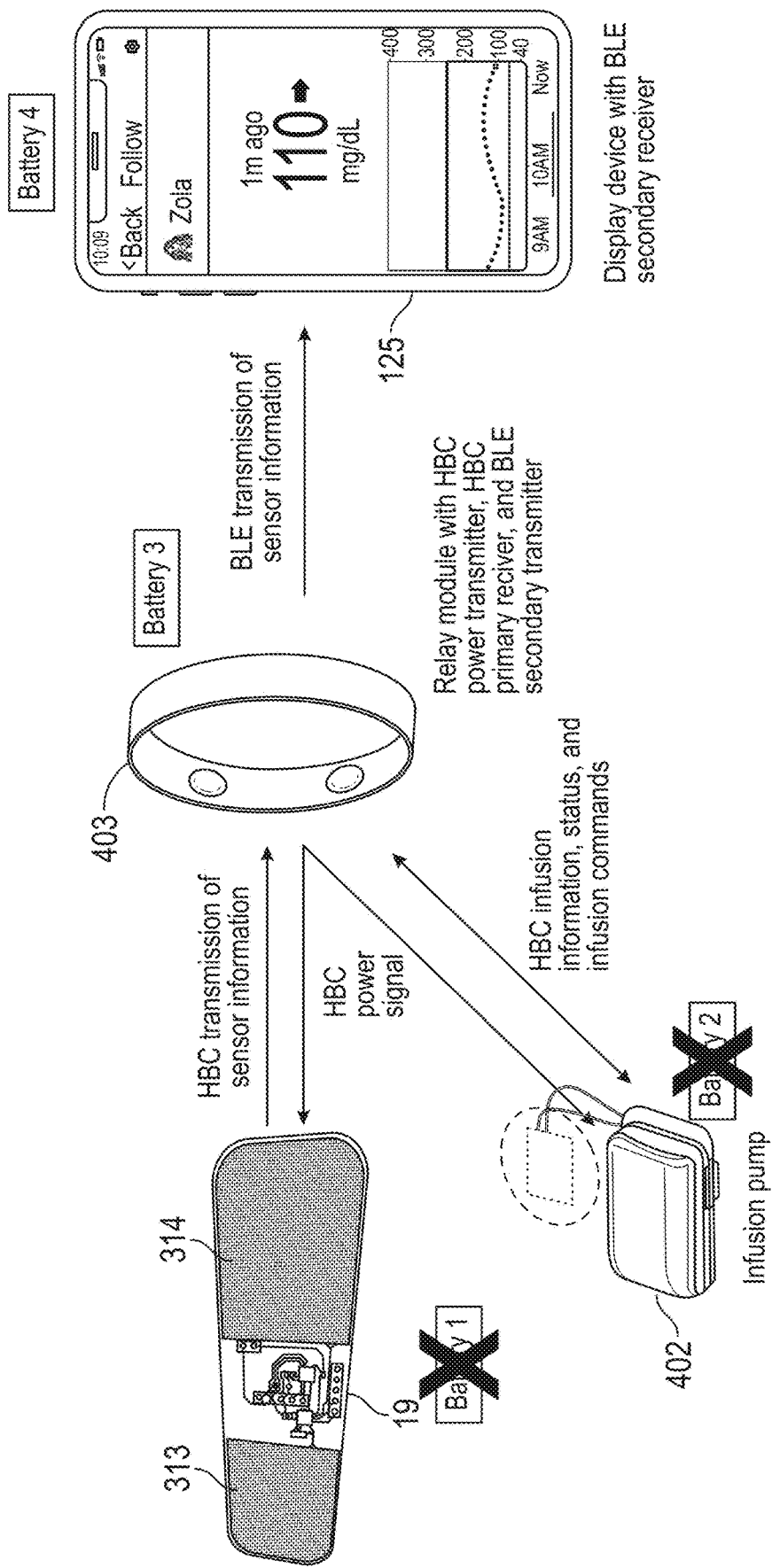
FIG. 7A illustrates a sixteenth analyte sensor system comprising a sensor unit and a display device configured for human body communication, and also an infusion pump, according to some embodiments.
Figure 7B:
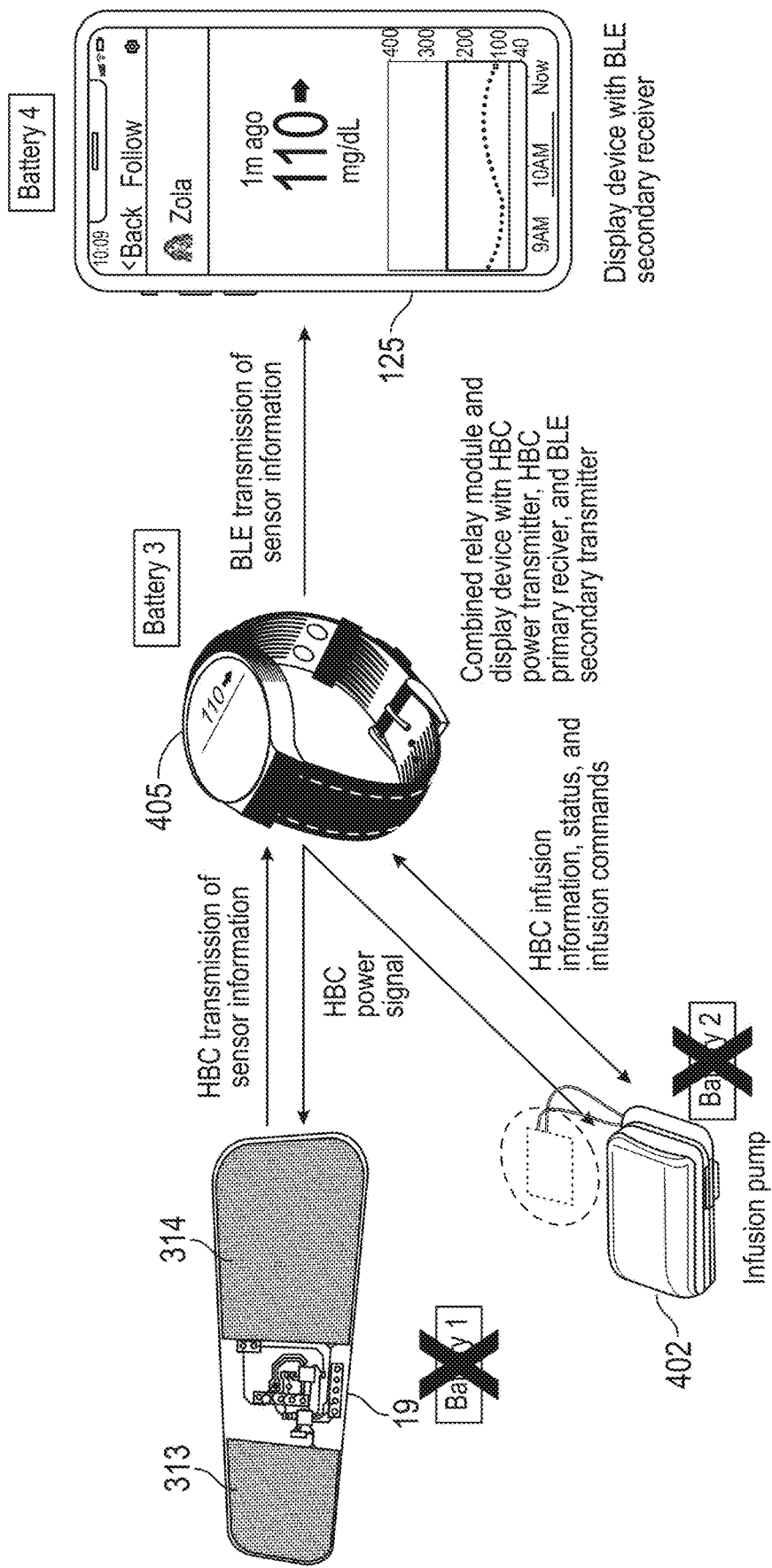
FIG. 7B illustrates a seventeenth analyte sensor system comprising a sensor unit and a display device configured for human body communication, and also an infusion pump, according to some embodiments.

FIG. 7A illustrates a sixteenth analyte sensor system comprising a sensor unit and a display device configured for human body communication, and also an infusion pump, according to some embodiments. FIG. 7B illustrates a seventeenth analyte sensor system comprising a sensor unit and a display device configured for human body communication, and also an infusion pump, according to some embodiments. FIGS. 7A and 7B illustrate embodiments that apply the principles described above to systems that include not only sensing capabilities but also therapeutic capabilities. A common example is a glucose sensor and an insulin infusion pump used at the same time. In the system of FIG. 7A, a wrist band 403 supplies power using HBC for both the sensor electronics module 19 and the infusion pump 402. The wrist band 403 may function as a relay module to display device 125 for sensor information received via HBC from the sensor electronics module 19. The wrist band 403 may also receive infusion pump status information from the infusion pump 402. The wrist band 403 may further contain processing power to process sensor information received from the sensor electronics module 19 and use that information to intelligently control the actions of the infusion pump 402.

The embodiment of FIG. 7B may function similarly to the embodiment of FIG. 7A, but in the embodiment of FIG. 7B the wrist band is implemented as a display device in addition to a relay module and power source.

General Interpretive Principles for the Present Disclosure

Various aspects of the novel systems, apparatuses, and methods are described more fully hereinafter with reference to the accompanying drawings. The teachings disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel systems, apparatuses, and methods disclosed herein, whether implemented independently of or combined with any other aspect of the disclosure. For example, a system or an apparatus may be implemented, or a method may be practiced using any one or more of the aspects set forth herein. In addition, the scope of the disclosure is intended to cover such a system, apparatus or method which is practiced using other structure, functionality, or structure and functionality in addition to or other than the various aspects of the disclosure set forth herein. It should be understood that any aspect disclosed herein may be set forth in one or more elements of a claim. Although some benefits and advantages of the preferred aspects are mentioned, the scope of the disclosure is not intended to be limited to particular benefits, uses, or objectives. The detailed description and drawings are merely illustrative of the disclosure rather than limiting, the scope of the disclosure being defined by the appended claims and equivalents thereof.

With respect to the use of plural vs. singular terms herein, those having skill in the art can translate from the plural to the singular and/or from the singular to the plural as is appropriate to the context and/or application. The various singular/plural permutations may be expressly set forth herein for sake of clarity.

When describing an absolute value of a characteristic or property of a thing or act described herein, the terms "substantial," "substantially," "essentially," "approximately," and/or other terms or phrases of degree may be used without the specific recitation of a numerical range. When applied to a characteristic or property of a thing or act described herein, these terms refer to a range of the characteristic or property that is consistent with providing a desired function associated with that characteristic or property.

In those cases where a single numerical value is given for a characteristic or property, it is intended to be interpreted as at least covering deviations of that value within one significant digit of the numerical value given.

If a numerical value or range of numerical values is provided to define a characteristic or property of a thing or act described herein, whether or not the value or range is qualified with a term of degree, a specific method of measuring the characteristic or property may be defined herein as well. In the event no specific method of measuring the characteristic or property is defined herein, and there are different generally accepted methods of measurement for the characteristic or property, then the measurement method should be interpreted as the method of measurement that would most likely be adopted by one of ordinary skill in the art given the description and context of the characteristic or property. In the further event there is more than one method of measurement that is equally likely to be adopted by one of ordinary skill in the art to measure the characteristic or property, the value or range of values should be interpreted as being met regardless of which method of measurement is chosen.

It will be understood by those within the art that terms used herein, and especially in the appended claims (e.g., bodies of the appended claims) are intended as "open" terms unless specifically indicated otherwise (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

In those instances where a convention analogous to "at least one of A, B, and C" is used, such a construction would include systems that have A alone, B alone, C alone, A and B together without C, A and C together without B, B and C together without A, as well as A, B, and C together. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include A without B, B without A, as well as A and B together."

Various modifications to the implementations described in this disclosure can be readily apparent to those skilled in the art, and generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

What is claimed is:

1. A physiological parameter monitoring system comprising:
   a transcutaneous or subcutaneous sensor configured to generate a sensor output signal;
   sensor electronics connected or connectable to the sensor with a wired connection;
   a primary sensor information transmitter connected or connectable to the sensor electronics with a wired connection, the primary sensor information transmitter having or being configured to have at least a portion thereof positioned at a first location adjacent to and/or in contact with the epidermis of a body of a host during a sensor session, the primary sensor information transmitter further configured to wirelessly transmit sensor information generated by or derived from the sensor output signal using human body communication;
   a relay module comprising:
      a primary sensor information receiver, the primary sensor information receiver having or being configured to have at least a portion thereof positioned at a second location adjacent to and/or in contact with the epidermis of the body of the host during the sensor session, the primary sensor information receiver further configured to wirelessly receive the sensor information from the primary sensor information transmitter using human body communication, and
      a secondary sensor information transmitter connected or connectable to the primary sensor information receiver with a wired connection and configured to wirelessly transmit sensor information previously received by the primary sensor information receiver from the primary sensor information transmitter; and
   a first display device comprising a display and a secondary sensor information receiver configured to wirelessly receive the sensor information from the secondary sensor information transmitter, wherein:
      the first display device is further configured to send a power signal to the relay module for powering the relay module; and
      the relay module is configured to relay the power signal to the sensor electronics for powering the sensor electronics.

2. The system of claim 1, wherein the secondary sensor information transmitter and the secondary sensor information receiver both comprise Bluetooth modules.

3. The system of claim 2, wherein the second location is a wrist of the host.

4. The system of claim 1, wherein the first display device comprises a smartphone.

5. A physiological parameter monitoring system comprising:
- a sensor configured to generate a sensor output signal;
- sensor electronics connected or connectable to the sensor with a wired connection;
- a first primary sensor information transmitter connected or connectable to the sensor electronics with a wired connection and configured to wirelessly transmit first sensor information generated by or derived from the sensor output signal using human body communication;
- a second primary sensor information transmitter connected or connectable to the sensor electronics with a wired connection and configured to wirelessly transmit second sensor information generated by or derived from the sensor output signal;
- a first display device comprising a display and a first primary sensor information receiver configured to wirelessly receive the first sensor information from the first primary sensor information transmitter using human body communication; and
- a second display device comprising a display and a second primary sensor information receiver, wherein:
  - the second display device different from the first display device;
  - the second primary sensor information receiver is configured to wirelessly receive the second sensor information from the second primary sensor information transmitter via a communication protocol different from human body communication; and
  - the second primary sensor information transmitter is configured to wirelessly transmit the second sensor information to the second primary sensor information receiver upon a determination that the first primary sensor information receiver did not receive the first sensor information.

6. The system of claim 5, wherein the second primary sensor transmitter and the second primary sensor information receiver both comprise a Bluetooth module.

7. A physiological parameter monitoring apparatus comprising:
- a sensor configured to generate a sensor output signal relating to a host;
- sensor electronics operably connected or connectable to the sensor; and
- a transmitter operably connected or connectable to the sensor electronics, the transmitter comprising:
- a first conductive contact positioned on a first side of the sensor electronics and operably connected to the sensor electronics; and
- a second conductive contact positioned on a second side of the sensor electronics and operably connected to the sensor electronics, wherein:
  - the sensor electronics is configured to apply a signal across the first and second conductive contacts to wirelessly transmit sensor information generated by or derived from the sensor output signal using human body communication;
  - the sensor electronics, the first conductive contact, and the second conductive contact are affixed to a common substrate; and
  - the common substrate comprises:
    - a first predetermined thickness for providing a first offset between the first conductive contact and a tissue of the host; and
    - a second predetermined thickness for providing a second offset between the second conductive contact and the tissue of the host, the second predetermined thickness different from the first predetermined thickness.

8. The apparatus of claim 7, wherein the common substrate comprises an adhesive or printed circuit board (PCB).

9. The apparatus of claim 7, wherein the sensor electronics is positioned between the first conductive contact and the second conductive contact.

10. The apparatus of claim 7, wherein the first conductive contact comprises a metal plate that is or is configured to be capacitively coupled to the epidermis of the host.

11. The apparatus of claim 7, wherein the second conductive contact comprises a metal plate that is or is configured to be capacitively coupled to the epidermis of the host.

12. The apparatus of claim 7, wherein the first conductive contact is covered with a first insulating film and wherein the second conductive contact is covered with a second insulating film.

13. The apparatus of claim 12, wherein the first insulating film is thinner than the second insulating film.

* * * * *